United States Patent
Lo et al.

(10) Patent No.: US 10,006,087 B2
(45) Date of Patent: Jun. 26, 2018

(54) MARKERS FOR PRENATAL DIAGNOSIS AND MONITORING

(71) Applicant: The Chinese University of Hong Kong, Shatin, N.T. (CN)

(72) Inventors: Yuk-Ming Dennis Lo, Homantin (CN); Rossa Wai Kwun Chiu, Shatin (CN); Stephen Siu Chung Chim, Quarry Bay (CN); Nancy Bo Yin Tsui, Kowloon (CN)

(73) Assignee: The Chinese University of Hong Kong, Shatin, N.T. (HK)

( * ) Notice: Subject to any disclaimer, the term of this patent is extended or adjusted under 35 U.S.C. 154(b) by 27 days.

(21) Appl. No.: 14/685,343

(22) Filed: Apr. 13, 2015

(65) Prior Publication Data

US 2015/0284800 A1    Oct. 8, 2015

Related U.S. Application Data

(62) Division of application No. 12/754,450, filed on Apr. 5, 2010, now abandoned, which is a division of application No. 11/378,598, filed on Mar. 17, 2006, now Pat. No. 7,718,367.

(60) Provisional application No. 60/663,293, filed on Mar. 18, 2005.

(51) Int. Cl.
  *C07H 21/04* (2006.01)
  *C12Q 1/68* (2018.01)
  *C12Q 1/6883* (2018.01)

(52) U.S. Cl.
  CPC ..... *C12Q 1/6883* (2013.01); *C12Q 2600/156* (2013.01); *C12Q 2600/158* (2013.01); *C12Q 2600/16* (2013.01)

(58) Field of Classification Search
  None
  See application file for complete search history.

(56) References Cited

U.S. PATENT DOCUMENTS

| 5,629,147 | A | 5/1997 | Asagari et al. |
| 7,235,359 | B2 | 6/2007 | Lo et al. |
| 2003/0124529 | A1 | 7/2003 | Oxvig |
| 2004/0203037 | A1* | 10/2004 | Lo ............ C12Q 1/6883 435/6.17 |
| 2007/0054278 | A1 | 3/2007 | Cargill |
| 2008/0233583 | A1 | 9/2008 | Fisher et al. |
| 2010/0016173 | A1 | 1/2010 | Nagalla et al. |
| 2013/0095482 | A1 | 4/2013 | Oxvig et al. |

FOREIGN PATENT DOCUMENTS

| CN | 1469932 | 1/2004 |
| WO | 2002/04678 | 1/2002 |
| WO | 2002/55985 | 7/2002 |
| WO | 2004/65629 | 8/2004 |
| WO | 2005/21793 | 3/2005 |

OTHER PUBLICATIONS

Poon (Annals of New York Academy of Science, 945:207-210, 2001).
Lo et al. (Nature Medicine, vol. 13, No. 2, pp. 218-223, Feb. 2007).
Kido (Genomics, vol. 17, pp. 256-259, 1993).
Banzola et al. (Prenat. Diagn., vol. 28, pp. 1262-1267, 2008).

* cited by examiner

*Primary Examiner* — Jeanine A Goldberg
(74) *Attorney, Agent, or Firm* — Kilpatrick Townsend & Stockton LLP

(57) ABSTRACT

Methods and kits are provided for diagnosing, monitoring, or predicting preeclaimpsia in a pregnant woman, trisomy 18 and trisomy 21 in a fetus, as well as for detecting pregnancy in a woman, by quantitatively measuring in the maternal blood the amount of one or more RNA species derived from a set of genetic loci and comparing the amount of the RNA species with a standard control.

9 Claims, 11 Drawing Sheets

MARKERS FOR PRENATAL DIAGNOSIS AND MONITORING

CROSS-REFERENCE TO RELATED APPLICATIONS

This application is a divisional of U.S. application Ser. No. 12/754,450, filed Apr. 5, 2010, which is a divisional of U.S. application Ser. No. 11/378,598, filed Mar. 17, 2006, now U.S. Pat. No. 7,718,367, which claims priority to U.S. Patent Application Ser. No. 60/663,293, filed Mar. 18, 2005, the contents of which are herein incorporated by reference in the entirety.

REFERENCE TO SUBMISSION OF A SEQUENCE LISTING

This application includes a Sequence Listing as a text file named "SEQ_80015-939025" created Jun. 17, 2015 and containing 30,743 bytes. The material contained in this text file is incorporated by reference in its entirety for all purposes.

BACKGROUND OF THE INVENTION

Prenatal diagnosis has been routinely conducted using cells isolated from the fetus through procedures such as chorionic villus sampling (CVS) or amniocentesis. These conventional methods are, however, invasive and present an appreciable risk to both the mother and the fetus despite most careful handling (Tabor et al., *Lancet* 1:1287-1293, 1986).

Alternatives to these invasive approaches have been developed for prenatal screening, e.g., to detecting fetal abnormalities, following the discoveries that several types of fetal cells can be found in maternal circulation (Johansen et al., *Prenat. Diagn.* 15:921-931, 1995) and more importantly, circulating cell-free fetal DNA can be detected in maternal plasma and serum (Lo et al., *Lancet* 350:485-487, 1997). The amount of fetal DNA in maternal blood has been shown to be sufficient for genetic analysis without complex treatment of the plasma or serum, in contrast to the necessary steps for isolating and enriching fetal cells. Fetal rhesus D (RhD) genotyping (Lo et al., *N Engl. J. Med.* 339:1734-1738, 1998), fetal sex determination (Lo et al., *Hum. Genet.* 90:483-488, 1993), and diagnosis of several fetal disorders (Amicucci et al., *Clin. Chem.* 46:301-302, 2000; Saito et al., *Lancet* 356:1170, 2000; and Chiu et al., *Lancet* 360:998-1000, 2002) have since been achieved by detecting fetal DNA in maternal blood using a polymerase chain reaction (PCR)-based technique.

In addition, quantitative abnormalities of fetal DNA in maternal plasma/serum have also been reported in preeclampsia (Lo et al., *Clin. Chem.* 45:184-188, 1999 and Zhong et al., *Am. J. Obstet. Gynecol.* 184:414-419, 2001), fetal trisomy 21 (Lo et al., *Clin. Chem.* 45:1747-1751, 1999 and Zhong et al. *Prenat. Diagn.* 20:795-798, 2000) and hyperemesis gravidarum (Sekizawa et al., *Clin. Chem.* 47:2164-2165, 2001). Detection of fetal nucleic acid in maternal blood for prenatal genetic analysis is also disclosed in U.S. Pat. No. 6,258,540.

When analyzing fetal DNA, investigators have often used Y chromosomal markers, which are only present in male fetuses, as a fetal-specific marker. This approach has limited the application of this technology to the 50% of pregnant women who are carrying male fetuses. Further, the use of other genetic polymorphisms has also increased the complexity of fetal DNA-based analyses. The discovery of fetal RNA in maternal plasma offers a possible new approach that circumvents these limitations (Poon et al., *Clin. Chem.* 46:1832-1834, 2000).

More recently, U.S. patent application Ser. No. 09/876,005 discloses non-invasive techniques based on detection of fetal/placental RNA in maternal blood. Further, U.S. patent application Ser. No. 10/759,783 discloses certain placental expressed mRNA markers (e.g., human chorionic gonadotropin β subunit and human corticotropin releasing hormone) that can be used for the detection of pregnancy and pregnancy-related disorders such as preeclampsia, fetal chromosomal aneuploidy, and pre-term labor. Various other RNA species of placental origin have also been detected in maternal blood, see, e.g., Oudejans et al., *Clin Chem.* 2003, 49(9):1445-1449, and Go et al., *Clin. Chem.* 2004, 50(8): 1413-1414. The present invention discloses additional fetal/placenta-derived RNA species, shown in Tables 1-6, that are found in maternal blood and can be used as markers for detecting pregnancy, or for genotyping the fetus, or for diagnosing, monitoring, and predicting preeclampsia and fetal chromosomal aneuploidy such as trisomy 18 and trisomy 21. Thus, the present invention provides additional tools for non-invasive prenatal diagnosis and alternative means for pregnancy detection.

BRIEF SUMMARY OF THE INVENTION

In the first aspect, the present invention relates to a method for diagnosing, monitoring, or predicting preeclampsia in a pregnant woman. This method comprises the following steps: first, quantitatively determining the amount of one or more RNA species in a biological sample obtained from the pregnant woman. The RNA species are independently selected from RNA derived from genetic loci consisting of IGFBP3, ABP1, FN1, SLC21A2, KIAA0992, TIMP3, LPL, INHBA, LEP, ADAM12, PAPPA, PAPPA2, and SIGLEC6, and the biological sample is blood, washing from the reproductive tract, urine, saliva, amniotic fluid, or chorionic villus. Second, comparing the amount of the RNA species from the first step to a standard control representing the amount of the RNA species in the corresponding sample from an average non-preeclamptic pregnant woman. An increase or a decrease in the amount of the RNA species from the standard control indicates preeclampsia or an increased risk of developing preeclampsia.

In some embodiments, the RNA species is derived from ADAM12, PAPPA2, FN1, INHBA, LEP, or SIGLEC6, and an increase in the amount of the RNA species from the standard control indicates preeclampsia or an increased risk of developing preeclampsia. In other embodiments, the RNA species is derived from PAPPA and a decrease in the amount of the RNA species from the standard control indicates preeclampsia or an increased risk of developing preeclaimpsia.

In some embodiments, the first step comprises using a reverse transcriptase polymerase chain reaction (RT-PCR). Optionally, this first step further comprises using mass spectrometry following RT-PCR. In other embodiments, the first step comprises using a polynucleotide hybridization method, or using a primer extension reaction.

In some embodiments, the woman being examined is during the first trimester of gestation. In other embodiments, the woman is during the second or third trimester of gestation.

In some embodiments, the blood is fractionated and the plasma fraction is analyzed. In other embodiments, the blood is fractionated and the serum fraction is analyzed. In some embodiments, the increase in the amount of RNA from the standard control is more than 2-fold. In other embodiments, the decrease in the amount of RNA from the standard control is more than 50%.

A kit for diagnosing, monitoring, or predicting preeclampsia in a pregnant woman is also provided. This kit comprises the following: (i) PCR primers for quantitatively determining the amount of one or more RNA species in a biological sample obtained from the pregnant woman, wherein the RNA species is independently selected from RNA derived from genetic loci consisting of IGFBP3, ABP1, FN1, SLC21A2, KIAA0992, TIMP3, LPL, INHBA, LEP, ADAM12, PAPPA, PAPPA2, and SIGLEC6, and wherein the biological sample is blood, washing from the reproductive tract, amniotic fluid, urine, saliva, or chorionic villus; and (ii) a standard control representing the amount of the RNA species in the corresponding sample from an average non-preeclamptic pregnant woman.

In the second aspect, the present invention relates to a method for detecting the presence of a fetus with trisomy 18 in a pregnant woman. This method comprises the following steps: first, quantitatively determining the amount of the RNA species derived from genetic locus RPL17 in a biological sample obtained from the pregnant woman. The biological sample is blood, washing from the reproductive tract, amniotic fluid, urine, saliva, or chorionic villus. Second, comparing the amount of the RPL17 RNA from the first step to a standard control representing the amount of the RPL17 RNA in the corresponding sample from an average pregnant woman carrying a chromosomally normal fetus. A deviation in the amount of the RNA species from the standard control indicates an increased risk of having a fetus with trisomy 18.

In some embodiments, an increase in the amount of the RPL17 RNA from the standard control indicates an increased risk of having a fetus with trisomy 18; whereas in other cases, a decrease in the amount of the RPL17 RNA from the standard control may indicate an increased risk of having a fetus with trisomy 18.

In some embodiments, the first step comprises using a reverse transcriptase polymerase chain reaction (RT-PCR). Optionally, this first step further comprises using mass spectrometry following RT-PCR. In other embodiments, the first step comprises using a polynucleotide hybridization method, or using a primer extension reaction.

In some embodiments, the woman being examined is during the first trimester of gestation. In other embodiments, the woman is during the second or third trimester of gestation.

In some embodiments, the blood is fractionated and the plasma fraction is analyzed. In other embodiments, the blood is fractionated and the serum fraction is analyzed. In some embodiments, the increase in the amount of RNA from the standard control is more than 2-fold. In other embodiments, the decrease in the amount of RNA from the standard control is more than 50%.

A kit for detecting the presence of a fetus with trisomy 18 in a pregnant woman is also provided. This kit comprises the following: (i) PCR primers for quantitatively determining the amount of RNA derived from genetic locus RPL17, wherein the biological sample is blood, washing from the reproductive tract, amniotic fluid, urine, saliva, or chorionic villus; and (ii) a standard control representing the amount of the RPL17 RNA in the corresponding sample from an average pregnant woman carrying a chromosomally normal fetus.

In a third aspect, the present invention relates to a method for detecting the presence of a fetus with trisomy 21 in a pregnant woman. The method comprises the following steps of: first, quantitatively determining the amount of one or more RNA species in a biological sample obtained from the pregnant woman. The RNA species is independently selected from RNA species derived from genetic loci consisting of COL6A1, COL6A2, SOD1, APP, BTG3, ATP5J, ADAMTS1, BACE2, DSCR5, ITSN1, PLAC4, ATP5O, LOC90625, EFEMP1, and TFRC, whereas the biological sample is blood, washing from the reproductive tract, urine, saliva, amniotic fluid, or chorionic villus. Second, comparing the amount of the RNA species from the first step to a standard control representing the amount of the RNA species in the corresponding sample from an average pregnant woman with a chromosomally normal fetus. An increase or a decrease in the amount of RNA species from the standard control indicates an increased risk of having a fetus with trisomy 21.

In some embodiments, the RNA species is derived from ADAMTS1, APP, ATP5O, EFEMP1, or TFRC, and an increase in the amount of RNA species from the standard control indicates an increased risk of having a fetus with trisomy 21.

In some embodiments, the first step comprises using a reverse transcriptase polymerase chain reaction (RT-PCR). Optionally, this first step further comprises using mass spectrometry following RT-PCR. In other embodiments, the first step comprises using a polynucleotide hybridization method, or using a primer extension reaction.

In some embodiments, the woman being examined is during the first trimester of gestation. In other embodiments, the woman is during the second or third trimester of gestation.

In some embodiments, the blood is fractionated and the plasma fraction is analyzed. In other embodiments, the blood is fractionated and the serum fraction is analyzed. In some embodiments, the increase in the amount of RNA from the standard control is more than 2-fold. In other embodiments, the decrease in the amount of RNA from the standard control is more than 50%.

A kit for detecting the presence of a fetus with trisomy 21 in a pregnant woman is also provided. This kit comprises the following: (i) PCR primers for quantitatively determining the amount of one or more RNA species in a biological sample obtained from the pregnant woman, wherein the RNA species is independently selected from RNA derived from genetic loci consisting of COL6A1, COL6A2, SOD1, APP, BTG3, ATP5J, ADAMTS1, BACE2, DSCR5, ITSN1, PLAC4, ATP5O, LOC90625, EFEMP1, and TFRC, and wherein the biological sample is blood, washing from the reproductive tract, amniotic fluid, urine, saliva, or chorionic villus; and (ii) a standard control representing the amount of the RNA species in the corresponding sample from an average pregnant woman carrying a chromosomally normal fetus.

In a fourth aspect, the present invention relates to a method for detecting pregnancy in a woman. The method comprises the following steps of: first, quantitatively determining the amount of one or more RNA species in a biological sample obtained from the woman. The RNA species is independently selected from RNA species derived from genetic loci consisting of COL6A1, COL6A2, SOD1, ATP5O, ADAMTS1, DSCR5, and PLAC4, whereas the biological sample is blood, washing from the reproductive tract, amniotic fluid, urine, saliva, or chorionic villus. Second, comparing the amount of the RNA species from the first step to a standard control representing the amount of the RNA species in the corresponding sample from an average non-pregnant woman. An increase or a decrease in the amount of RNA species from the standard control indicates pregnancy.

In some embodiments, the RNA species is derived from COL6A1, COL6A2, ATP5O, or PLAC4, and an increase in the amount of RNA species from the standard control indicates pregnancy.

In some embodiments, the first step comprises using a reverse transcriptase polymerase chain reaction (RT-PCR). Optionally, this first step further comprises using mass spectrometry following RT-PCR. In other embodiments, the first step comprises using a polynucleotide hybridization method, or using a primer extension reaction.

In some embodiments, the woman being examined is during the first trimester of gestation. In other embodiments, the woman is during the second or third trimester of gestation.

In some embodiments, the blood is fractionated and the plasma fraction is analyzed. In other embodiments, the blood is fractionated and the serum fraction is analyzed. In some embodiments, the increase in the amount of RNA from the standard control is more than 2-fold. In other embodiments, the decrease in the amount of RNA from the standard control is more than 50%.

A kit for detecting pregnancy in a woman is also provided. This kit comprises the following: (i) PCR primers for quantitatively determining the amount of one or more RNA species in a biological sample obtained from the pregnant woman, wherein the RNA species is independently selected from RNA derived from genetic loci consisting of COL6A1, COL6A2, SOD1, ATP5O, ADAMTS1, DSCR5, and PLAC4, and wherein the biological sample is blood, washing from the reproductive tract, amniotic fluid, urine, saliva, or chorionic villus; and (ii) a standard control representing the amount of the RNA species in the corresponding sample from an average non-pregnant woman.

DEFINITIONS

Figure 1A:
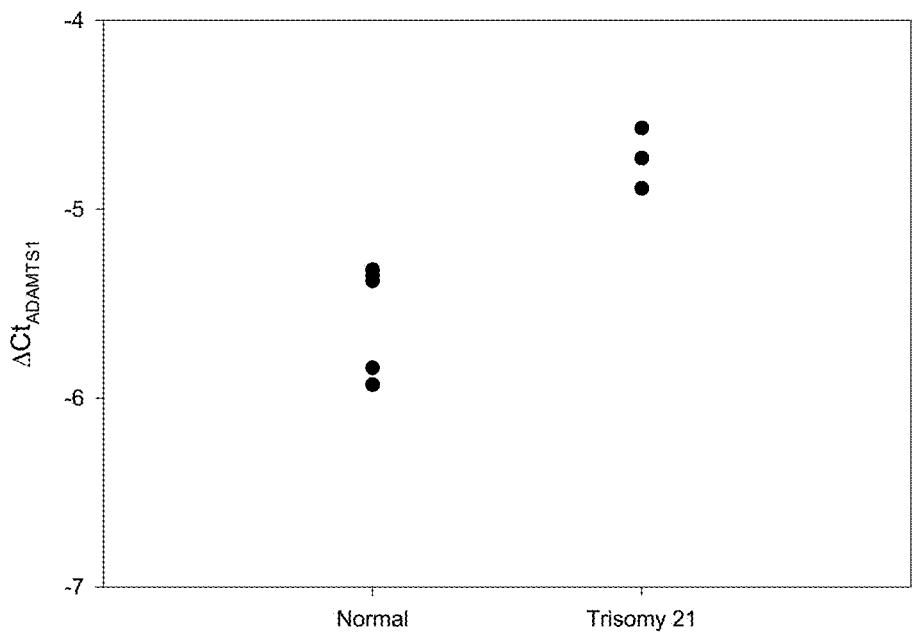
FIG. 1. Comparison of placental tissue levels of RNA transcripts in first-trimester trisomy 21 and control pregnancies. (A) ADAMTS1 mRNA. (B) APP mRNA. Each ● represents one subject.

The term "an RNA species derived from a genetic locus" as used herein refers to a polymer of ribonucleotides that has a sequence corresponding to at least a portion of a preselected location in the human genome. An "RNA species" in this application may or may not encode for a protein product, as its sequence may encompass non-coding sequence or include only a partial open reading frame.

The term "fetal," "placental derived," or "placental expressed" as used herein describes the origin of certain RNA species that are detectable in a biological sample from a pregnant woman, e.g., blood. In other words, a fetal RNA species is one that has been transcribed from a fetal DNA sequence. Furthermore, a placental derived or placental expressed RNA species is one that is found in the placenta and transcribed from a fetal DNA sequence.

The term "washing of reproductive tract" as used herein refers to any liquid or solution that has been collected following the rinse or wash of the reproductive tract of a pregnant woman or a woman who is being tested for possible pregnancy.

The term "preeclampsia" as used herein refers to a condition that occurs during pregnancy, the main symptom of which is various forms of high blood pressure often accompanied by the presence of proteins in the urine and edema (swelling). Preeclampsia, sometimes called toxemia of pregnancy, is related to a more serious disorder called "eclampsia," which is preeclampsia together with seizure. These conditions usually develop during the second half of pregnancy (after 20 weeks), though they may develop shortly after birth or before 20 weeks of pregnancy.

The term "primer extension reaction" as used herein refers to any polymerization process mediated by the action of a nucleotide polymerase, e.g., a DNA polymerase, by extending a predetermined polynucleotide sequence that is at least partially complementary to a template sequence under appropriate conditions.

The term "chromosomal aneuploidy" as used herein refers to a state of chromosomal abnormality where the number of chromosomes is not an exact multiple of the usual haploid number: frequently, there is either an additional chromosome or one missing. The most common case of a chromosomal aneuploidy is a trisomy, where a single additional chromosome is present. For example, trisomy 18 is a chromosomal abnormality where a third chromosome 18 is found in a cell, whereas a third chromosome 21 is present in the cells of a patient suffering from trisomy 21.

In contrast to aneuploidy, "chromosomally normal" describes the state where the number of chromosomes is an exact multiple of the haploid number, such as twice the number of chromosomes found in a haploid, and each chromosome is present in the same number (except the sex chromosomes in the case of, e.g., male humans, where two different sex chromosomes, X and Y, are present at one copy each).

The term "blood" as used herein refers to a blood sample or preparation from a pregnant woman or a woman being tested for possible pregnancy. The term encompasses whole blood or any fractions of blood having varying concentrations or even no hematopoietic or any other types of cells or cellular remnants of maternal or fetal origin, including platelets. Examples of "blood" include plasma and serum. A blood sample that is essentially free of cells is also referred to as "acellular," where generally no platelets are present.

The term "average," as used in the context of describing a pregnant woman who is non-preeclamptic, or carries a chromosomally normal fetus, refers to certain characteristics, such as the level of fetal/placental derived RNA found in maternal blood, that is representative of a randomly selected group of women who are non-preeclamptic or are carrying chromosomally normal fetuses. This selected group should comprise a sufficient number of women such that the average level of fetal/placental derived RNA transcribed from genetic loci (which may be coding for a particular fetal protein or may be non-coding) reflects, with reasonable accuracy, the level of RNA in the general population of healthy pregnant women with healthy fetuses. In addition, the selected group of women should have a similar gestational age to that of a woman whose blood is tested for indication of preeclampsia or fetal chromosomal aneuploidy such as trisomy 18 and trisomy 21. The preferred gestational age for practicing the present invention may vary, depending on the disorder that is being screened for. For example, a pregnant woman is screened for the risk of preeclampsia preferably during the second trimester of the pregnancy, whereas fetal chromosomal aneuploidy is preferably screened for and diagnosed as early as possible. Moreover, the preferred gestational age for testing may also depend on the RNA marker used in testing, as certain markers may be more readily detectable during some stages of gestation than in others stages.

The term "average" may be used similarly to refer to the amount of specified RNA species that is representative of the amount found in the blood of a randomly selected group of healthy non-pregnant women.

IGFBP3, ABP1, FN1, SLC21A2, KIAA0992, TIMP3, LPL, INHBA, LEP, SIGLEC6, RPL17, COL6A1, COL6A2, SOD1, APP, BTG3, ATP5J, ADAMTS1, BACE2, DSCR5, ITSN1, PLAC4, LOC90625, ATP5O, EFEMP1, and TFRC, as used herein, refer to the genes or proposed open reading frames (including their variants and mutants) and their polynucleotide transcripts as exemplified by the sequences set forth in GenBank Accession Nos. provided in Tables 2, 4, and 6. In some context, these terms may also be used to refer to the polypeptides encoded by these genes or open reading frames.

"Standard control" as used herein refers to a sample suitable for the use of a method of the present invention, in order for quantitatively determining the amount of RNA transcript, e.g., COL6A1, COL6A2, APP, ATP5O, or LEP. Such a sample contains a known amount of the fetal/placental derived RNA species that closely reflects the average level of such RNA in an average pregnant woman. Similarly, a "standard control" may be derived from an average healthy non-pregnant woman.

"An increase or a decrease in the amount of mRNA from the standard control" as used herein refers to a positive or negative change in amount from the standard control. An increase is preferably at least 2-fold, more preferably at least 5-fold, and most preferably at least 10-fold. Similarly, a decrease is preferably at least 50%, more preferably at least 80%, and most preferably at least 90%.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"PCR primers" as used herein refer to oligonucleotides that can be used in a polymerase chain reaction (PCR) to amplify a nucleotide sequence originated from an RNA transcript derived from a genetic locus, such as COL6A1, COL6A2, APP, ATP5O, or LEP. At least one of the PCR primers for amplification of an RNA sequence derived from an above-named locus should be sequence-specific for the said locus.

DETAILED DESCRIPTION OF THE INVENTION

I. Introduction

The present invention provides, for the first time, methods and kits for diagnosing, monitoring, or predicting preeclampsia and fetal chromosomal aneuploidy such as trisomy 18 and trisomy 21 in pregnant women, as well as for detecting pregnancy in women, by analyzing the level of one or more of several fetal/placental derived RNA species, i.e., those with sequences set forth in Tables 1-6, present in the women's blood.

According to the invention, the amount of these RNA transcripts of fetal/placental origin in a maternal blood sample can be quantitatively determined, preferably following an amplification procedure, e.g., reverse transcriptase polymerase chain reaction (RT-PCR). The amount of one or more of these RNA species is then compared to a standard control having an RNA level of the same species that is representative of an average pregnant woman without these pregnancy-related disorders at a similar gestational age. An increase or decrease in the RNA level indicates the presence of or an increased risk of developing the disorders. The present invention thus provides a novel approach for diagnosis of preeclampsia and fetal chromosomal aneuploidy such as trisomy 18 and trisomy 21, which is non-invasive as well as gender- and polymorphism-independent.

Relying on the same methodology, by comparing the level of one or more of the RNA species transcribed from these genetic loci in a woman's blood to an established control value obtained from average non-pregnant woman, the present invention may be used to detect pregnancy.

Although fetal/placental expressed RNA has been used as markers for prenatal diagnosis and monitoring, see, e.g., U.S. patent application Ser. Nos. 09/876,005 and 10/759,783, the identification of any particular RNA species as a suitable marker for this purpose is a finding of unpredictable nature, as not all species of RNA expressed in placenta can be detected in maternal blood. For instance, the present inventors have been unable to detect certain fetal/placental derived RNA species in the maternal blood. Some exemplary species that are undetectable include: NADH dehydrogenase (ubiquitnone) flavoprotein 3, 10 kDa (NDUFV3); alpha-fetoprotein (AFP); hemoglobin, epsilon 1 (HBE1); and phospholipase A2, group IIA (platelets, synovila fluid) (PLA2G2A).

II. Preparation of Blood Samples

A. Obtaining Blood Samples

The first step of practicing the present invention is to obtain a biological sample, e.g., a blood sample, from a pregnant woman at a gestational age suitable for testing using a method of the present invention, or from a woman who is being tested for possible pregnancy. The suitable gestational age may vary depending on the disorder tested and sometimes the RNA marker used, as discussed above. Collection of blood from a woman is performed in accordance with the standard protocol hospitals or clinics generally follow. An appropriate amount of peripheral blood, e.g., between 3-20 ml, is collected and maybe stored according to standard procedure prior to further preparation.

B. Preparing Plasma or Serum Samples

The serum or plasma of a woman's blood is suitable for the present invention and can be obtained by well known methods. For example, a woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum is obtained through centrifugation following blood clotting. Centrifugation is typically conducted at an appropriate speed, e.g., 1,500-3,000×g, in a chilled environment, e.g., at a temperature of about 4-10° C. Plasma or serum may be subject to additional centrifugation steps before being transferred to a fresh tube for RNA extraction. In certain applications of this invention, plasma or serum may be the preferred sample types. In other applications of the present invention, whole blood may be preferable. Yet in other applications, other fractions of blood may be preferable.

III. Quantitative Determination of the Amount of RNA in a Woman's Blood

A. Extraction of RNA

There are numerous methods for extracting RNA from a biological sample. The general methods of RNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain RNA from a blood sample from a woman. Combinations of more than one of these methods may also be used.

It is preferable in some applications that all or most of the contaminating DNA be eliminated from the RNA preparations. Thus, careful handling of the samples, thorough treatment with DNase, and proper negative controls in the amplification and quantification steps should be used.

B. PCR-Based Quantitative Determination of RNA Level

Once RNA is extracted from a woman's blood sample, the amount of RNA derived from a genetic locus of interest, e.g., COL6A1, COL6A2, APP, ATP5O, or LEP, may be quantified. The preferred method for determining the RNA level is an amplification-based method, e.g., by PCR.

Prior to the amplification step, a DNA copy (cDNA) of the RNA of interest must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is typically cycled through a denaturing region, a primer annealing region, and an extension reaction region automatically. In some protocols, the annealing region and the extension reaction region are merged. Machines specifically adapted for this purpose are commercially available.

Although PCR amplification of the target RNA is typically used in practicing the present invention. One of skill in the art will recognize, however, that amplification of these RNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of RNA markers in maternal blood. For a review of branched-DNA signal amplification for direct quantification of nucleic acid sequences in clinical samples, see Nolte, *Adv. Clin. Chem.* 33:201-235, 1998.

C. Other Quantitative Methods

The RNA species of interest can also be detected using other standard techniques, well known to those of skill in the art. Although the detection step is typically preceded by an amplification step, amplification is not required in the methods of the invention. For instance, the RNA species of interest may be identified by size fractionation (e.g., gel electrophoresis), whether or not preceded or followed by an amplification step. After running a sample in an agarose or polyacrylamide gel and labeling with ethidium bromide according to well known techniques (see, e.g., Sambrook and Russell, supra), the presence of a band of the same size as the standard control is an indication of the presence of a target RNA, the amount of which may then be compared to the control based on the intensity of the band. Alternatively, oligonucleotide probes specific to RNA transcribed from a genetic locus, e.g., COL6A1, COL6A2, APP, ATP5O, or LEP, can be used to detect the presence of such RNA species and indicate the amount of RNA in comparison to the standard control, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, In situ *Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques and the detection is not a critical aspect of the present invention. Nucleic acid probes capable of specifically hybridizing to a target nucleic acid, i.e., the RNA species of interest or the amplified DNA, can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on the sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange high performance liquid chromatography (HPLC) as described in Pearson and Regnier, *J. Chrom.*, 255:137-149, 1983.

IV. Establishing a Standard Control

In order to establish a standard control, a group of healthy pregnant women carrying healthy fetuses should first be selected. These women should be of similar gestational age, which is within the appropriate time period of pregnancy for screening of conditions such as preeclampsia and fetal chromosomal aneuploidies (including trisomy 18 or trisomy 21) using the methods of the present invention. Similarly, a standard control is established using samples from a group of healthy non-pregnant women.

The health status of the selected pregnant women and the fetuses they are carrying should be confirmed by well established, routinely employed methods including but not limited to monitoring blood pressure of the women, recording the onset of labor, and conducting fetal genetic analysis using CVS and amniocentesis.

Furthermore, the selected group of healthy pregnant women carrying healthy fetuses or healthy non-pregnant women must be of a reasonable size, such that the average amount of RNA derived from the genetic loci named in this application calculated from the group can be reasonably regarded as representative of the normal or average amount among the general population of healthy women carrying healthy fetuses or healthy non-pregnant women. Preferably, the selected group comprises at least 10 women.

Once an average value is established for the amount of fetal/placental derived RNA based on the individual values found in each women of the selected group, this value is considered a standard for the RNA species. Any blood sample that contains a similar amount of RNA of the same species can thus be used as a standard control. A solution containing RNA species of interest with a concentration of the established average of the same species can also be artificially assembled and serve as a standard control.

The following examples are provided by way of illustration only and not by way of limitation. Those of skill in the art will readily recognize a variety of non-critical parameters that could be changed or modified to yield essentially similar results.

EXAMPLES

The following examples are provided by way of illustration only and not by way of limitation. Those of skill in the art will readily recognize a variety of non-critical parameters that could be changed or modified to yield essentially the same or similar results.

Example 1: Genetic Loci on Chromosome 21 or 18 with Expression in Placental Tissues Methods
Subjects Placental tissue and blood samples were collected with informed consent from pregnant women during the first trimester, who attended the Department of Obstetrics and Gynecology at the Prince of Wales Hospital, Hong Kong. The study was approved by the Clinical Research Ethics Committee.

Sample Preparation for Microarray Analysis

Five first-trimester placental tissue samples were obtained from pregnant women by chorionic villus sampling (CVS) before therapeutic terminations. Fetal karyotypes in all cases were subsequently confirmed to be normal. The placental tissue samples were stored in RNAlater™ (Ambion®, Austin, Tex.) immediately upon collection and kept at −80° C. until RNA extraction. Six milliliters of maternal peripheral blood were collected concurrently at the time of tissue collection and stored in PAXgene™ Blood RNA Tubes (PreAnalytiX, Hombrechtikon, Switzerland). Total RNA from placental tissues were extracted with Trizol Reagent (Invitrogen, Carlsbad, Calif.) and purified with the RNeasy mini-kit (Qiagen, Hilden, Germany) following manufacturers' protocols. Total RNA from peripheral blood was extracted by the PAXgene™ Blood RNA Kit (PreAnalytiX, Hombrechtikon, Switzerland) according to manufacturer's instructions, with the inclusion of DNase treatment (RNase-Free DNase Set, Qiagen, Hilden, Germany).

Gene Expression Analysis by High-Density Oligonucleotide Microarrays

For each sample, ten micrograms of the extracted RNA were labeled and hybridized to the GeneChip® Human Genome U133A and U133B Arrays (Affymetrix, Santa Clara, Calif.) according to the manufacturer's instructions. After hybridization, each array was washed and stained in a GeneChip® Fluidics Station 400 (Affymetrix, Santa Clara, Calif.). The chips were scanned with the GeneArray Scanner (Affymetrix, Santa Clara, Calif.) and analyzed using the GeneChip® Microarray Suite 5.0 (Affymetrix).

Real-Time Quantitative RT-PCR

One-step real-time quantitative RT-PCR (QRT-PCR) was used for the quantitative measurement of RNA transcripts in placental tissues and maternal blood samples. QRT-PCR assays for the detection of the house-keeping gene, glyceraldehyde-3-phosphate dehydrogenase (GAPDH) have been described previously (Ng et al. 2002). Sequences of the primers (Proligo, Singapore) and fluorescent probes (Applied Biosystems, Foster City, Calif., USA) of the other studied genes are shown in Table 1A. For placental tissues and maternal buffy coat analyses, relative quantification was employed wherein the studied transcript levels were normalized to the corresponding GAPDH mRNA levels.

The QRT-PCR reactions were set up according to the manufacturer's instructions (EZ rTth RNA PCR reagent set, Applied Biosystems) in a reaction volume of 25 µl. The QRT-PCR assays were carried out in a combined thermal cycler and fluorescent detector (ABI Prism 7900HT, Applied Biosystems). For all transcripts, the PCR primers and the fluorescent probes were used at concentrations of 300 nM and 100 nM, respectively. Before performing QRT-PCR, contaminating DNA in the placental tissue RNA extracts was removed by DNase I digestion (Invitrogen, Carlsbad, Calif.) according to the manufacturer's recommendations. 17 ng of extracted placental RNA was used for amplification. Multiple negative water blanks were included in every analysis.

The thermal profiles used were as follows: the reaction was initiated at 50° C. for 2 min for the included uracil N-glycosylase to act, followed by reverse transcription at 60° C. for 30 min. After a 5-min denaturation at 95° C., 40 cycles of PCR were carried out using denaturation at 92° C. for 15 s and 1 min annealing/extension at 58° C.

Quantitative Assessment of Placental Expressed Transcripts in Maternal Blood

Maternal whole blood samples from normal pregnant women were collected into EDTA tubes. After centrifugation of the blood samples at 1,600 g for 10 min at 4° C., the buffy coat and plasma fractions were carefully transferred into separate polypropylene tubes. The plasma samples were re-centrifuged at 16,000 g for 10 min at 4° C. Supernatants were collected into fresh polypropylene tubes. RNA extraction from the harvested maternal plasma was performed as previously described (Ng et al., 2002). RNA was similarly extracted from 0.3 mL of the buffy coat fraction.

QRT-PCR assays for the studied transcripts were carried out with the same conditions described above. Five microliters of the extracted plasma RNA or 10 ng of the buffy coat RNA were used for each QRT-PCR reaction. Absolute quantification was used to determine the transcript concentrations in plasma samples. Calibration curves were prepared by serial dilutions of high performance liquid chromatography-purified single stranded synthetic DNA oligonucleotides (Proligo, Singapore) spanning the full lengths of the amplicons, with concentrations ranging from $1\times10^7$ copies to $1\times10^1$ copies. Absolute concentrations of the transcripts in plasma were expressed as copies/ml of plasma. The sequences of the synthetic DNA oligonucleotides are shown in Table 1B. Results for the buffy coat fractions were expressed by relative quantification based on normalization to GAPDH.

Statistical Analysis

Statistical analysis was performed using the Sigma Stat 2.03 software (SPSS).

Results

Identification of Placental Expressed Genes by High-Density Oligonucleotide Microarrays Gene expression profiles of five first-trimester CVS samples were obtained by independent microarray analysis of each individual tissue sample. Among the ~22,000 well-characterized transcripts detectable by the Human Genome U133A and U133B Arrays (Affymetrix), a total of 7226 gene transcripts were expressed in the CVS samples. We have previously reported that circulating DNA in the plasma of normal individuals is predominantly derived from hematopoietic cells (Lui et al., 2002). Thus, we hypothesize that much of the background maternal nucleic acids in maternal blood also originate from the hematopoietic compartment. As we aim to identify placenta-expressed transcripts amongst the circulating RNA molecules in maternal plasma, we further obtained the gene expression profiles of maternal whole blood and compared these profiles with those of the corresponding placental tissues using the GeneChip® Microarray Suite 5.0 software (Affymetrix). Placental expressed transcripts in early pregnancy were identified by selecting transcripts whose expression levels were "increased" in the CVS tissues when compared to the corresponding whole blood samples in all five sets of comparisons. After this procedure, transcripts that were expressed in maternal blood cells to a higher or similar degree as that of placental tissues were eliminated. Thus, this analysis has resulted in the identification of a panel of 1245 transcripts with relative placental specificity in the first trimester of pregnancy.

Selection of Genetic Loci Encoded on Chromosome 21 or 18 with Expression in Placental Tissues Among the panel of transcripts with relative placental specificity as identified by the approach described above, we further sought for transcripts that were derived from genes positioned on chromosome 21. Thirteen genes that are located on chromosome 21 have been identified and are summarized in Table 2A. This gene selection strategy is based on the reasoning that the altered gene dosage as a result of the presence of an additional chromosome 21 in the genome of a fetus with trisomy 21, may lead to aberrant expression of genes located on chromosome 21. As we have previously shown that the placenta is an important source of circulating fetal RNA in maternal plasma (Ng et al., 2003), aberrant placental tissue expression of the targeted genes as a result of trisomy 21 may be reflected by aberrant concentrations of the said transcripts in maternal blood. Thus, one approach for the noninvasive prenatal detection of fetal trisomy 21 through circulating fetal/placental derived RNA analysis is based on the detection of abnormal blood concentrations of those selected transcripts in women with fetuses affected by trisomy 21 in comparison to that in women conceived with a normal fetus.

A similar strategy had been applied for the identification of gene markers potentially useful for the noninvasive prenatal assessment of trisomy 18. The gene expression profiles of both the CVS and maternal whole blood samples were analyzed by the Human Genome U133B Arrays (Affymetrix). A panel of transcripts with preferential expression in CVS with respect to maternal blood was identified with the use of the same screening criteria described above. Placental expressed genes which are located on chromosome 18 were selected from the panel of transcripts with relative placental specificity. Within the panel, the transcript with the highest expression level in CVS was selected and shown in Table 2B.

Validation of Microarray Results by Real-Time QRT-PCR

Placental tissue expression of the markers identified from the microarray-based strategy described above were verified by one-step real-time QRT-PCR. First trimester CVS tissues from ten normal pregnancies and three trisomy 21 pregnancies were measured for GAPDH mRNA and the selected transcripts listed in Tables 2A and 2B. The relative mRNA levels of the studied genes were normalized to the corresponding GAPDH levels using the equation:

$$\Delta Ct_X = Ct_{GAPDH} - Ct_X$$

where Ct represents the threshold cycle which is the number of PCR cycles required for the accumulated fluorescence of the QRT-PCR reaction of a sample to reach a predetermined threshold intensity. $\Delta Ct_X$ is the normalized mRNA level of a studied transcript, X; $Ct_{GAPDH}$ is the Ct value of GAPDH mRNA; and $Ct_X$ is the Ct value of the transcript, X. As the Ct value is inversely proportional to the logarithm of the amount of template mRNA, greater $\Delta Ct_X$ values represent higher mRNA levels. The studied transcripts have been confirmed to be expressed and detectable in the CVS tissues collected from normal as well as pregnancies involving a trisomy 21 fetus.

Figure 1B:
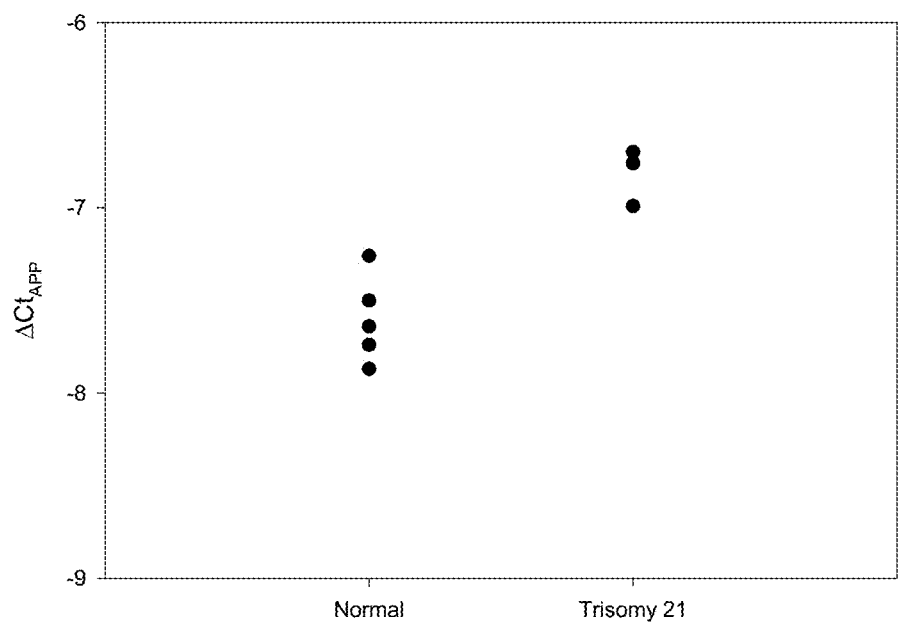

Statistically significant up-regulations in the placental tissue expression of ADAMTS1 mRNA (FIG. 1A) (Mann-Whitney test, P=0.036) and APP mRNA (FIG. 1B) (Mann-Whitney test, P=0.036) were found in the CVS tissues collected from trisomy 21 pregnancies in comparison to normal pregnancies. These data confirmed our hypothesis that genes located on the trisomic chromosome are associated with quantitative aberrations in placental tissue expression and thus, are potentially useful markers for the prenatal assessment of trisomy 21.

Detectability of the Placental Expressed Transcripts in Maternal Blood

Figure 2:
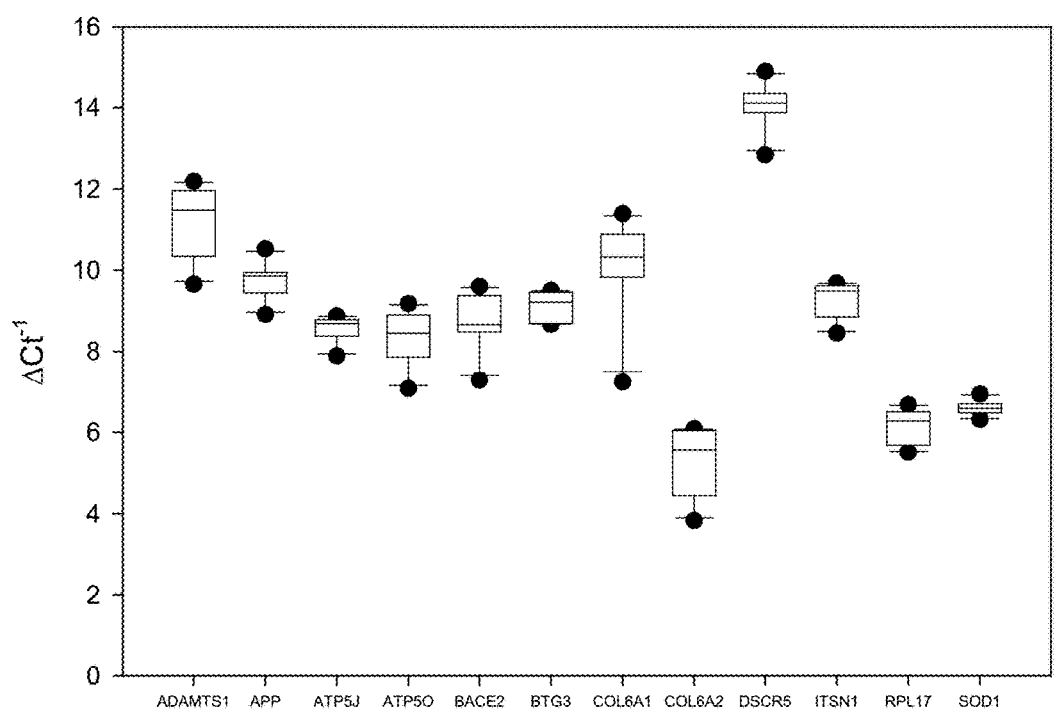
FIG. 2. Relative concentrations of placental expressed transcripts in maternal buffy coat. The lines inside the boxes denote the medians. The boxes mark the interval between the 25th and 75th percentiles. The whiskers denote the interval between the 10th and 90th percentiles. The filled circles mark the data points outside the 10th and 90th percentiles.
Figure 3A:
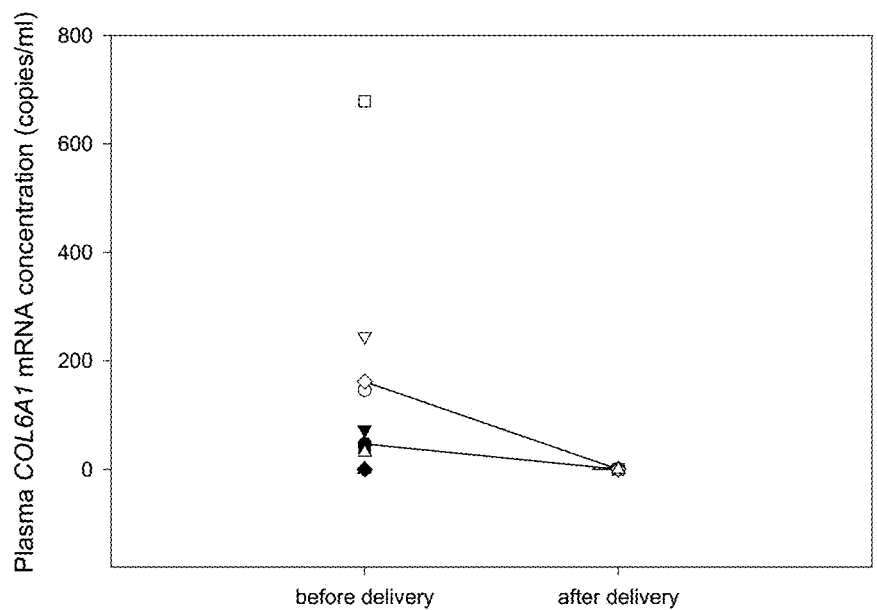
FIG. 3. Clearance of placental mRNA from maternal plasma after delivery. Maternal plasma concentrations of (A) COL6A1 mRNA and (B) COL6A2 mRNA before delivery and 24 hours after delivery. Each line represents the paired plasma samples obtained from one subject.
Figure 3B:
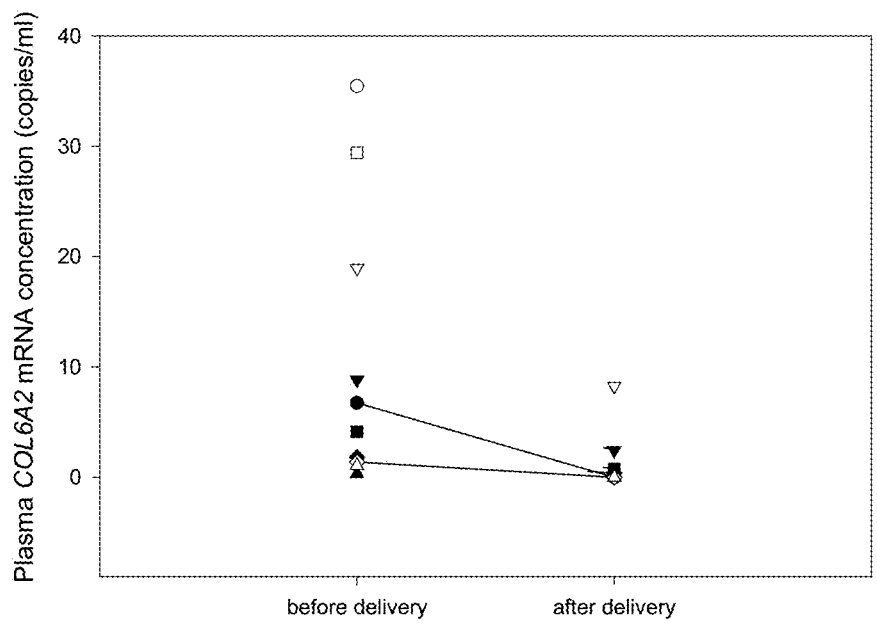

Detectability of some of the transcripts was assessed in buffy coat and plasma samples collected from women in the third trimester of pregnancy. All of the twelve studied transcripts were detectable in both the buffy coat (FIG. 2) and plasma samples (data not shown). To test for the pregnancy specificity of the transcripts, plasma samples from ten pregnant women before delivery and at 24 hours after delivery were also collected. FIGS. 3A and 3B reveal that both COL6A1 and COL6A2 mRNA were promptly cleared from the maternal plasma after delivery (Wilcoxon test, P<0.05 for both cases), while the corresponding plasma GAPDH mRNA levels remained unchanged (data not shown, Wilcoxon test, P=1.000). The post-delivery clearance of COL6A1 and COL6A2 mRNA from maternal plasma suggests that the placenta is the predominant tissue source of these transcripts.

Conclusion

Using a microarray-based approach, transcripts that are expressed in first trimester placental tissues were identified. Thirteen transcripts that are useful for the prenatal assessment of trisomy 21 were identified based on the selection of placental expressed genes that are located on chromosome 21. Similarly, an RNA marker that is useful for the prenatal assessment of trisomy 18 was identified through the selection of placental transcripts that are encoded on chromosome 18.

The detectability of the studied transcripts in both normal and aneuploid placental tissues were confirmed by real-time QRT-PCR. As examples, ADAMTS1 and APP mRNA were shown to be aberrantly expressed in placental tissues of trisomy 21 pregnancies. In addition, mRNA of all the targeted genes were found to be detectable in maternal buffy coat and plasma. These data confirm that our marker selection strategy enables the identification of RNA species that are aberrantly expressed in trisomy 21 placental tissues and are detectable in maternal circulation which would facilitate the development of strategies for the noninvasive prenatal diagnosis of fetal trisomy 21. For example, noninvasive prenatal assessment of trisomy 21 could be based on the detection of the aberrant concentrations of the RNA markers in maternal blood of trisomy 21 pregnancies in comparison to those of normal pregnancies. Alternatively, noninvasive prenatal diagnosis could be carried out based on the relative quantitative comparison of different molecular forms of one or more of the transcripts in maternal plasma. Similar applications can also be applied to trisomy 18 with the detection of RPL17 mRNA in maternal plasma.

Example 2: Genes with Increased Expression in Placentas of Trisomy 21 Pregnancies Compared with That of Normal Pregnancies Methods Subjects All placental tissue and blood samples in this study were collected with informed consent from women in the first trimester of pregnancy, who attended the Department of Obstetrics and Gynecology at the Prince of Wales Hospital, Hong Kong. The study was approved by the Clinical Research Ethics Committee.

In the first part of the study, placental tissue gene expression profiles of both the normal and trisomy 21 pregnancies were identified by oligonucleotide microarray. First-trimester placental tissue samples were obtained from pregnant women by chorionic villus sampling (CVS). Five women with normal pregnancies (gestational age range: 10-12 weeks) and three pregnant women conceived with trisomy 21 fetuses (gestational age range: 12-13 weeks) were recruited with the respective fetal karyotype subsequently confirmed. In the second part of the study, the gene expression profiles generated by the oligonucleotide microarray experiments were confirmed using QRT-PCR. CVS from three trisomy 21 pregnancies (gestational age range: 13-14 weeks) and 5 normal pregnant women (gestational age range: 9-13 weeks) were recruited for this part of the study.

Sample Preparation for Microarray Analysis

CVS samples were stored in RNAlater™ (Ambion®, Austin, Tex.) immediately upon collection and kept at −80° C. until RNA extraction. For the five pregnant women with normal pregnancies, six milliliters of maternal peripheral blood were collected concurrently at the time of tissue collection and stored in PAXgene™ Blood RNA Tubes (PreAnalytiX, Hombrechtikon, Switzerland). Total RNA from placental tissues were extracted with Trizol Reagent (Invitrogen, Carlsbad, Calif.) and purified with the RNeasy mini-kit (Qiagen, Hilden, Germany) following manufacturers' protocols. Total RNA from peripheral blood was extracted by the PAXgene™ Blood RNA Kit (PreAnalytiX, Hombrechtikon, Switzerland) according to manufacturer's instructions, with the inclusion of DNase treatment (RNase-Free DNase Set, Qiagen, Hilden, Germany).

Gene Expression Analysis by High-Density Oligonucleotide Microarrays

For each sample, ten micrograms of the extracted RNA were labeled and hybridized to the GeneChip® Human Genome U133A and U133B Arrays (Affymetrix, Santa Clara, Calif.) according to the manufacturer's instructions. After hybridization, each array was washed and stained in a GeneChip® Fluidics Station 400 (Affymetrix, Santa Clara, Calif.). The chips were scanned with the GeneArray Scanner (Affymetrix, Santa Clara, Calif.) and analyzed using the GeneChip® Microarray Suite 5.0 (Affymetrix).

Real-Time Quantitative RT-PCR

One-step real-time QRT-PCR was used for the quantitative measurement of mRNA transcripts in placental tissues and maternal plasma samples. QRT-PCR assays for the detection of the house-keeping gene, GAPDH have been described previously (Ng et al., 2002). Sequences of the primers (Proligo, Singapore) and TaqMan minor-groove-binding (MGB) fluorescent probes (Applied Biosystems, Foster City, Calif., USA) of the other studied genes are shown in Table 3. The mRNA quantities were expressed using relative quantifications wherein the studied transcript levels were normalized to the corresponding GAPDH mRNA levels.

The QRT-PCR reactions were set up according to the manufacturer's instructions (EZ rTth RNA PCR reagent set, Applied Biosystems) in a reaction volume of 25 µl. The QRT-PCR assays were carried out in a combined thermal cycler and fluorescent detector (ABI Prism 7900HT, Applied Biosystems). For all transcripts, the PCR primers and the fluorescent probes were used at concentrations of 300 nM and 100 nM, respectively. Before performing QRT-PCR, contaminating DNA in the extracted placental tissue RNA was removed by DNase I digestion (Invitrogen, Carlsbad, Calif.) according to the manufacturer's recommendations. 17 ng of placental RNA extracts was used for amplification. Multiple negative water blanks were included in every analysis.

The thermal profiles used for all of the studied transcripts were as follows: the reaction was initiated at 50° C. for 2 min for the included uracil N-glycosylase to act, followed by reverse transcription at 60° C. for 30 min. After a 5-min denaturation at 95° C., 40 cycles of PCR were carried out using denaturation at 92° C. for 15 s and 1 min annealing/extension at 58° C.

Quantitative Assessment of Trisomy 21 Associated Placental Transcripts in Maternal Blood Maternal whole blood samples from pregnant women were collected into EDTA tubes. After centrifugation of the blood samples at 1,600 g for 10 min at 4° C., plasma was carefully transferred into plain polypropylene tubes. The plasma samples were re-centrifuged at 16,000 g for 10 min at 4° C. Supernatants were collected into fresh polypropylene tubes. RNA extraction from the harvested maternal plasma was performed as previously described (Ng et al., 2002). QRT-PCR assays for the studied transcripts were carried out with conditions described above. Five microliters of the extracted plasma RNA were used for each QRT-PCR reaction.

Statistical Analysis

Statistical analysis was performed using the Sigma Stat 2.03 software (SPSS).

Results

Microarray-Based Identification of Genes with Aberrant Placental Tissue Expression in Aneuploid Pregnancies Gene expression profiles of the five first-trimester CVS samples collected from normal pregnancies were obtained by independent microarray analysis of each individual tissue sample. We have previously reported that circulating DNA in the plasma of normal individuals is predominantly derived from hematopoietic cells (Lui et al., 2002). Thus, we hypothesize that much of the background maternal nucleic acids in maternal blood also originate from the hematopoietic compartment. As the ultimate aim of the study was to identify placental expressed transcripts that are fetal specific amongst the circulating RNA molecules in maternal blood, we further obtained the gene expression profiles of paired maternal whole blood and compared these profiles with those of the corresponding CVS for the five normal pregnancy samples. GeneChip® Microarray Suite 5.0 software (Affymetrix) was used for the comparison. Transcripts with relative placental specificity were identified by selecting transcripts whose expression levels were 'increased' in the CVS tissues when compared to the corresponding whole blood samples in all five sets of comparisons. After these procedures, transcripts that were expressed in maternal blood cells to a higher or similar degree to that of CVS tissues were eliminated. This procedure has resulted in the identification of a panel of transcripts which are preferentially expressed in placental tissues.

In the next step, transcripts that are aberrantly expressed in placental tissues of aneuploid pregnancies were identified. Using the GeneChip® Microarray Suite 5.0 software (Affymetrix), expression profiles of three trisomy 21 CVS tissues were compared with the panel of genes with relative placental specificity identified from five gestational-age matched normal pregnancies as described above. Gene expression signals of the three aneuploid CVS samples were compared individually with that of each of the five normal CVS samples using the normal placental tissue expression profiles as baselines. A total of 15 comparisons were performed and the number of comparisons which showed up-regulated expression in the aneuploid placentas were counted (I-count) for each of the genes interrogated. The fold-changes in expression levels were calculated and were converted to $\log_2$ values (Signal Log Ratio, SLR). Transcripts were further selected if: (i) the transcripts were up-regulated in aneuploid placentas when compared to normal placentas to the extent where the Signal Log Ratio of at least 0.4 (1.3-fold change in expression); and (ii) the up-regulations were consistent where more than half of the comparisons revealed such up-regulations (I-count ≥8). Table 4 summarizes the microarray results of three transcripts, namely EGF-containing fibulin-like extracellular matrix protein 1 (EFEMP1), transferrin receptor p90 CD71 (TFRC), and ATP5O, which are preferentially expressed in placentas with the greatest extent of up-regulations among the gene panels for trisomy 21 pregnancies.

Validation of Microarray Results by Real-Time QRT-PCR

The three transcripts with aberrant placental tissue expression in trisomy 21 pregnancies as identified from the microarray experiments described above were verified by one-step real-time QRT-PCR. mRNA levels of the three transcripts and GAPDH were quantified in CVS tissues collected from three trisomy 21 and five normal pregnancies matched for gestational age. The relative mRNA levels of the studied genes were normalized to the corresponding GAPDH levels using the equation:

$$\Delta Ct_X = Ct_{GAPDH} - Ct_X$$

where Ct represents the threshold cycle which is the number of PCR cycles required for the accumulated fluorescence of the QRT-PCR reaction of a sample to reach a predetermined threshold intensity. $\Delta Ct_X$ is the normalized mRNA level of a studied transcript, X; $Ct_{GAPDH}$ is the Ct value of GAPDH mRNA; and $Ct_X$ is the Ct value of the transcript, X. As the Ct value is inversely proportional to the logarithm of the amount of template mRNA, greater $\Delta Ct_X$ values represent higher mRNA levels.

Figure 4A:
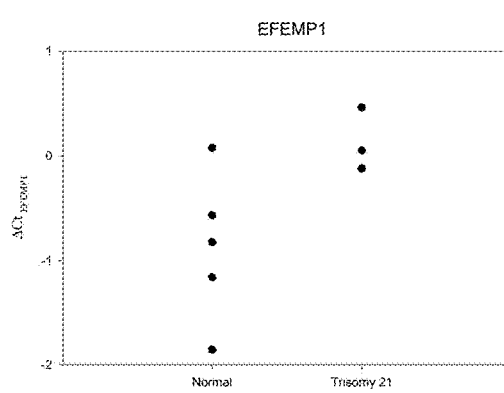
FIG. 4. Comparison of placental tissue levels of RNA transcripts in first-trimester trisomy 21 and control (normal) pregnancies. (A) EFEMP1 mRNA. (B) TFRC mRNA. (C) ATP5O mRNA. Each ● represents one subject. (D) Clearance of ATP5O mRNA from maternal plasma 24 hours after delivery. Each line represents the paired plasma samples obtained from one subject.
Figure 4B:
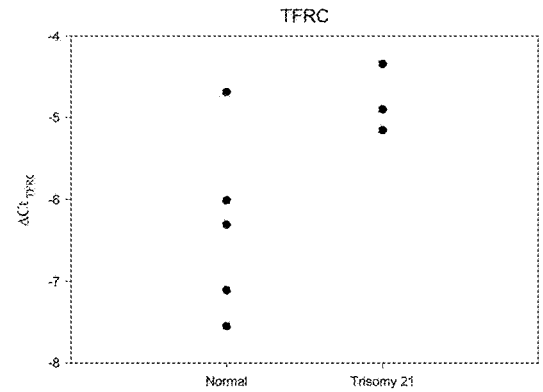
Figure 4C:
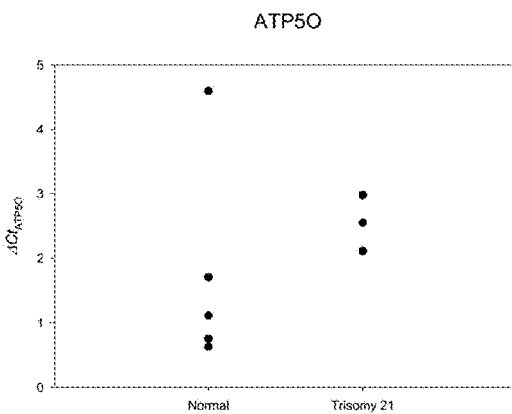

The QRT-PCR analysis revealed that EFEMP1 mRNA (FIG. 4A), TFRC mRNA (FIG. 4B) and ATP5O mRNA (FIG. 4C) were indeed up-regulated in the trisomy 21 CVS when compared to CVS collected from normal pregnancies. The aberrant placental tissue expression of the three transcripts is present in aneuploid pregnancies, thus demonstrates their utility as RNA markers for the prenatal investigation of trisomy 21.

Detectability of the RNA Markers in Maternal Plasma

Figure 4D:
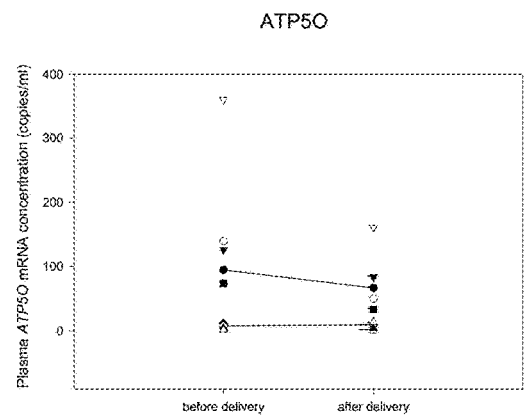

Plasma samples from normal pregnant women were measured for ATP5O mRNA. ATP5O mRNA is detectable in maternal plasma (FIG. 4D) with a statistically significant decrease in its concentration 24 hours after delivery (FIG. 4D; Wilcoxon, P<0.05). These data indicate that the placenta is an important tissue source of ATP5O mRNA in maternal plasma.

Conclusion

Using a microarray-based approach, transcripts with aberrant expressions in trisomy 21 placental tissues were identified. The three transcripts, EFEMP1, TFRC, and ATP5O, were identified by the microarray experiments and the aberrant nature of their expression in placental tissues of trisomy 21 pregnancies were further verified by QRT-PCR. These data thus indicate that the three transcripts are useful as RNA markers for the prenatal assessment of fetal trisomy 21. The detectability of ATP5O mRNA in maternal plasma indicates the suitability of this transcript for the noninvasive prenatal assessment of fetal trisomy 21. For example, noninvasive prenatal assessment of trisomy 21 could be based on the detection of the aberrant concentrations of the RNA markers in maternal plasma of trisomy 21 pregnancies in comparison to that of normal pregnancies.

Example 3: Genes with Aberrant Expression in Placentas of Pregnancies Affected by Preeclampsia Compared with That of Normal Pregnancies Methods
Subjects All placental tissue and blood samples in this study were collected with informed consent from women in the third trimester of pregnancy, who attended the Department of Obstetrics and Gynecology at the Prince of Wales Hospital, Hong Kong. The study was approved by the Clinical Research Ethics Committee.

In the first part of the study, placental tissue gene expression profiles of both normal and preeclamptic (PET) pregnancies were identified by oligonucleotide microarray. Placental tissues from 5 PET pregnant women (gestational age range: 37-40 weeks) and 5 healthy pregnant women (gestational age range: 38-40 weeks) were obtained immediately after cesarean section. Peripheral blood was collected immediately before delivery. In the second part of the study, the gene expression profiles generated from the oligonucleotide microarray experiments were confirmed using QRT-PCR. Placentas from 10 PET (gestational age range: 25-40 weeks) and 10 healthy pregnant women (gestational age range: 37-39 weeks) were collected immediately after cesarean delivery. Preeclampsia was defined on the basis of a sustained increase in diastolic blood pressure >110 mm Hg on one occasion or >90 mm Hg on two or more occasions at least 4 hours apart, with the presence of significant proteinuria in women with no history of hypertension. Significant proteinuria was defined as proteinuria >0.3 g/day or ≥2+ on dipstick testing in two clean-catch midstream urine specimens collected at least 4 hours apart.

Sample Preparation for Microarray Analysis

Placental tissue samples were stored in RNAlater™ (Ambion®, Austin, Tex.) immediately upon collection and kept at −80° C. until RNA extraction. Six milliliters of maternal peripheral blood were collected concurrently at the time of tissue collection and stored in PAXgene™ Blood RNA Tubes (PreAnalytiX, Hombrechtikon, Switzerland). Total RNA from placental tissues were extracted with Trizol Reagent (Invitrogen, Carlsbad, Calif.) and purified with the RNeasy mini-kit (Qiagen, Hilden, Germany) following manufacturers' protocols. Total RNA from peripheral blood was extracted by the PAXgene™ Blood RNA Kit (PreAnalytiX, Hombrechtikon, Switzerland) according to manufacturer's instructions, with the inclusion of DNase treatment (RNase-Free DNase Set, Qiagen, Hilden, Germany).

Gene Expression Analysis by High Density Oligonucleotide Microarrays

For each sample, ten micrograms of the extracted RNA were labeled and hybridized to the GeneChip® Human Genome U133A and U133B Arrays (Affymetrix, Santa Clara, Calif.) according to the manufacturer's instructions. After hybridization, each array was washed and stained in a GeneChip® Fluidics Station 400 (Affymetrix, Santa Clara, Calif.). The chips were scanned with the GeneArray Scanner (Affymetrix, Santa Clara, Calif.) and analyzed using the GeneChip® Microarray Suite 5.0 (Affymetrix).

Real-Time Quantitative RT-PCR

One-step real-time QRT-PCR was used for the quantitative measurement of mRNA transcripts in placental tissues and maternal plasma samples. QRT-PCR assays for the detection of the house-keeping gene, GAPDH have been described previously (Ng et al., 2002). Sequences of the primers and TaqMan minor-groove-binding (MGB) fluorescent probes (Applied Biosystems, Foster City, Calif., USA) of the other studied genes are shown in Table 5. The mRNA quantities were expressed using relative quantifications wherein the studied transcript levels were normalized to the corresponding GAPDH mRNA levels.

The QRT-PCR reactions were set up according to the manufacturer's instructions (EZ rTth RNA PCR reagent set, Applied Biosystems) in a reaction volume of 25 μl. The QRT-PCR assays were carried out in a combined thermal cycler and fluorescent detector (ABI Prism 7900HT, Applied Biosystems). For all of the studied transcripts, the PCR primers (Proligo) and the fluorescent probes (Applied Biosystems) were used at concentrations of 300 nM and 100 nM, respectively. Before performing QRT-PCR, contaminating DNA in the placental tissue RNA extracts was removed by DNase I digestion (Invitrogen, Carlsbad, Calif.) according to the manufacturer's recommendations. 17 ng of extracted placental RNA was used for amplification. Multiple negative water blanks were included in every analysis.

The thermal profiles used were as follows: the reaction was initiated at 50° C. for 2 min for the included uracil N-glycosylase to act, followed by reverse transcription at 60° C. for 30 min. After a 5-min denaturation at 95° C., 40 cycles of PCR were carried out using denaturation at 92° C. for 15 s and 1 min annealing/extension at 56° C.

Quantitative Assessment of Preeclampsia-Associated Placental Transcripts in Maternal Blood Maternal whole blood samples from pregnant women were collected into EDTA tubes. After centrifugation of the blood samples at 1,600 g for 10 min at 4° C., plasma was carefully transferred into plain polypropylene tubes. The plasma samples were re-centrifuged at 16,000 g for 10 min at 4° C. Supernatants were collected into fresh polypropylene tubes. RNA extraction from the harvested maternal plasma was performed as previously described (Ng et al., 2002). QRT-PCR assays for the studied transcripts were carried out with conditions described above. Five microliters of the extracted plasma RNA were used for each QRT-PCR reaction.

Statistical Analysis

Statistical analysis was performed using the Sigma Stat 2.03 software (SPSS).

Results

Microarray-Based Identification of Genes with Aberrant Placental Tissue Expression in Preeclamptic Pregnancies Our ultimate goal is to develop an approach for the investigation of PET through the detection of PET-associated transcripts in maternal blood. Therefore, our gene selection strategy would first entail the identification of transcripts which are preferentially expressed in the PET placentas but not in the maternal peripheral blood cells. This strategy was devised based on our previous finding that the placenta is an important source of circulating fetal RNA in maternal blood and the hematopoietic system is the main source of plasma DNA in normal individuals (Lui et al., 2002). Gene expression profiles of 5 PET placental tissue samples and their corresponding peripheral blood samples were determined by oligonucleotide microarray. To identify placental expressed genes, transcripts which were expressed in at least 4 of the 5 analyzed PET placental tissue samples were selected. Genes that were also expressed in maternal blood cells were then eliminated through the positive selection of transcripts whose expression levels were either "absent" in all of the 5 peripheral blood samples or "increased" in the placentas when compared to the corresponding whole blood samples in all of the five sets of paired placentas and maternal blood samples. Thus, transcripts that were expressed in a similar or greater extent in the maternal blood cells than the placental tissues were eliminated. These procedures resulted in the selection of a panel of transcripts which were preferentially expressed in placental tissues.

In the next step, transcripts with aberrant expression in PET placentas were identified. Expression profiles of placentas collected from 5 each of PET and normal pregnancies matched for gestational ages were compared using GeneChip® Microarray Suite 5.0 software (Affymetrix). Expression signals of the list of relatively placental specific genes identified from the 5 PET pregnancies as described above were compared individually with that of each of the 5 normal placental tissue samples using the normal placental tissue expression profiles as baselines. A total of 25 comparisons were performed and the number of comparisons which showed up-regulated expression in the PET placentas were counted (I-count) for each of the genes interrogated. The fold-changes in expression levels were calculated and were converted to $\log_2$ values (Signal Log Ratio, SLR). Transcripts were further selected if: (i) the transcripts were up-regulated in PET placentas when compared to normal placentas to the extent where the Signal Log Ratio of at least 0.4 (1.3-fold change in expression) and (ii) the up-regulations were consistent where more than half of the comparisons revealed such up-regulations (I-count ≥13). Table 6 summarizes the microarray results of the ten identified transcripts which are preferentially expressed in placentas with up-regulations in PET pregnancies.

Validation of Microarray Results by Real-Time QRT-PCR

The PET-related transcripts selected from the microarray analyses were verified by one-step real-time QRT-PCR. GAPDH mRNA concentrations were measured in placental tissues collected from ten each of PET and normal pregnancies matched for gestational age. The GAPDH mRNA levels were used to normalize the transcript levels between different samples. The expression levels of the ten transcripts identified by the microarray analyses were then assessed in the placental tissue samples of both groups of pregnancies. The relative mRNA levels of the studied genes were normalized to the corresponding GAPDH levels using the equation:

$$\Delta Ct_X = Ct_{GAPDH} - Ct_X$$

where Ct represents the threshold cycle which is the number of PCR cycles required for the accumulated fluorescence of the QRT-PCR reaction of a sample to reach a predetermined threshold intensity. $\Delta Ct_X$ is the normalized mRNA level of a studied transcript, X; $Ct_{GAPDH}$ is the Ct value of GAPDH mRNA; and $Ct_X$ is the Ct value of the transcript, X. As the Ct value is inversely proportional to the logarithm of the amount of template mRNA, greater $\Delta Ct_X$ values represent higher mRNA levels.

Figure 5A:
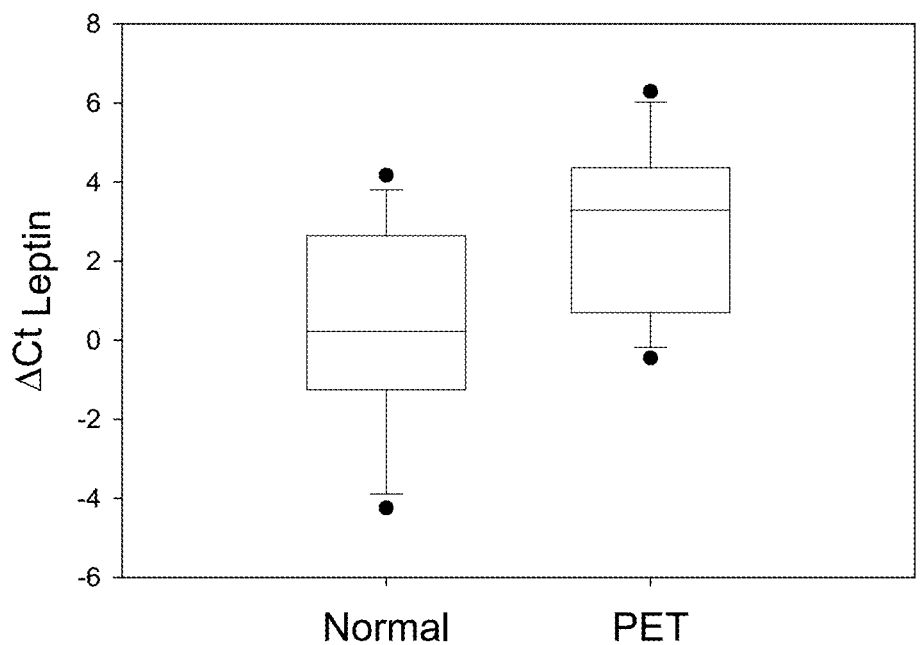
FIG. 5. Comparison of placental tissue levels of RNA transcripts in third-trimester preeclamptic (PET) and control pregnancies. (A) Leptin (LEP) mRNA. (B) SIGLEC6 mRNA. The lines inside the boxes denote the medians. The boxes mark the interval between the 25th and 75th percentiles. The whiskers denote the interval between the 10th and 90th percentiles. The filled circles mark the data points outside the 10th and 90th percentiles.
Figure 5B:
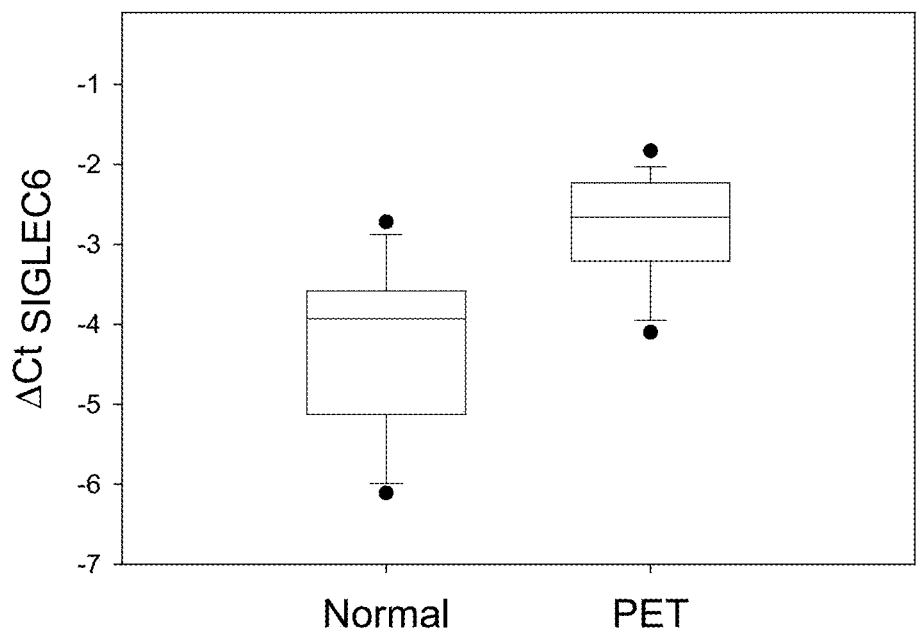

Leptin (LEP) and sialic acid binding Ig-like lectin 6 (SIGLEC6) mRNA were confirmed to be significantly up-regulated in PET placentas when compared with those of normal pregnancies by the QRT-PCR analyses (FIGS. 5A, and 5B for Leptin, and SIGLEC6 mRNA, respectively) (Mann-Whitney test, P <0.05 for both cases). These data confirm that our transcript selection strategy enables the identification of markers that are aberrantly expressed in PET placental tissues.

Detectability of the PET-Related RNA Markers in Maternal Plasma

Figure 6A:
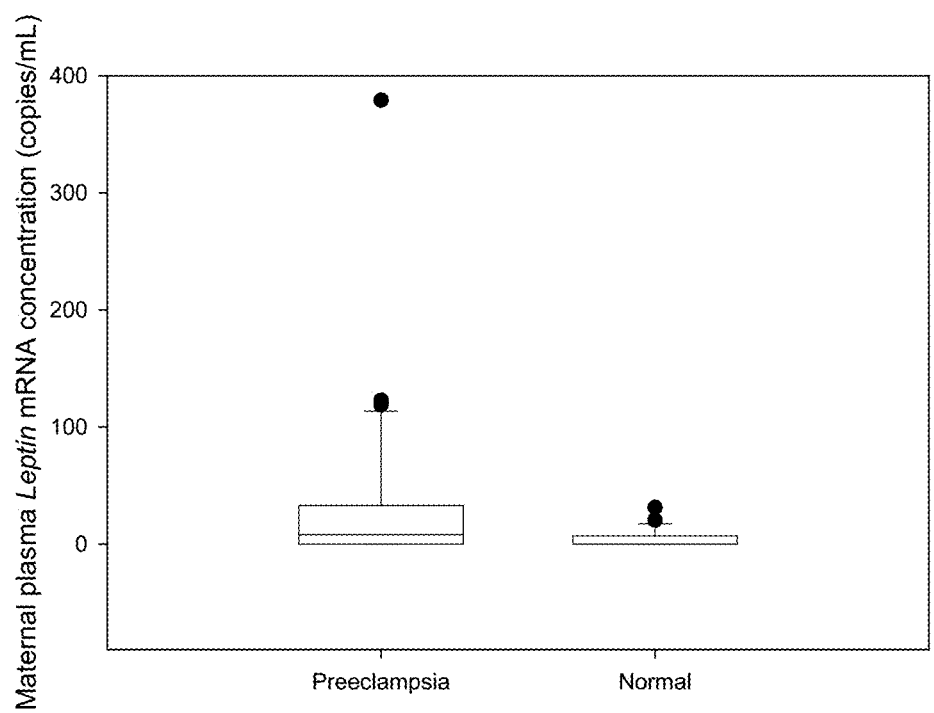
FIG. 6. Comparison of maternal plasma concentrations of (A) Leptin (LEP) mRNA and (B) INHBA mRNA in maternal plasma of preeclamptic and control pregnancies. The lines inside the boxes denote the medians. The boxes mark the interval between the 25th and 75th percentiles. The whiskers denote the interval between the 10th and 90th percentiles. The filled circles mark the data points outside the 10th and 90th percentiles.
Figure 6B:
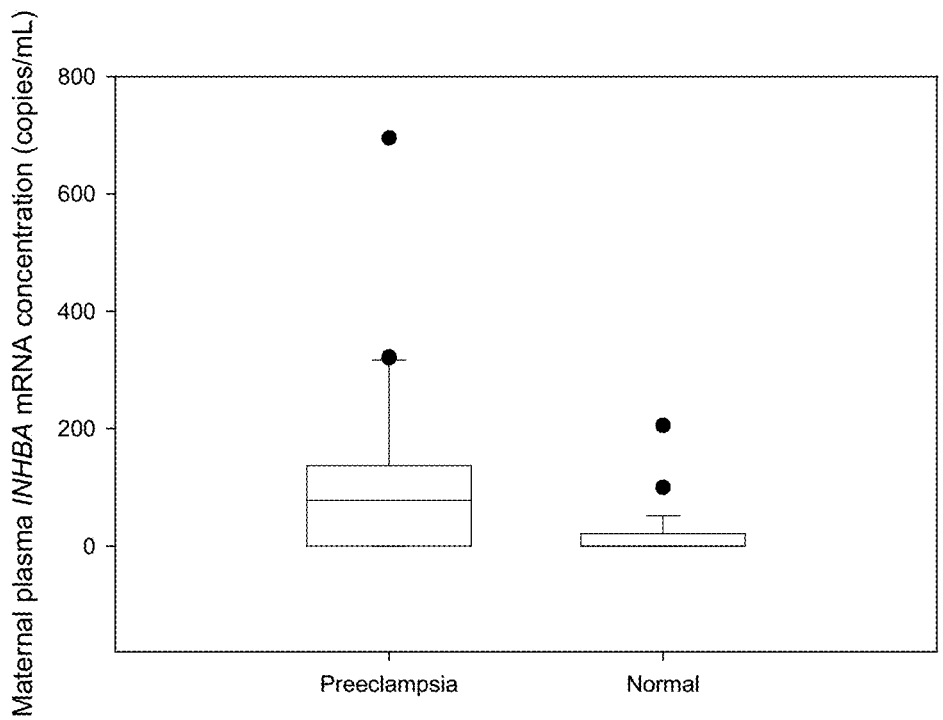

Plasma samples from 25 healthy and 26 PET-affected pregnancies in the third trimester were measured for LEP and INHBA mRNA by QRT-PCR. Maternal plasma concentrations for LEP and INHBA were significantly elevated in pregnancies affected by PET when compared with the uncomplicated pregnancies (LEP: FIG. 6A, Mann-Whitney, P=0.017; INHBA: FIG. 6B, Mann Whitney, P=0.006).

Conclusion

Using a microarray-based approach, transcripts with differential expression in PET placentas were identified and were considered as potential markers for the investigation of PET. Within the list of PET-associated transcripts identified by the micorarray analyses, ten transcripts that are most aberrantly expressed in PET placentas compared to that of normal pregnancies were selected. Real-time QRT-PCR confirmed that both LEP and SIGLEC6 expressions were significantly up-regulated in PET placentas when compared with normal placentas. Maternal plasma levels of INHBA and LEP were significantly higher in PET than uncomplicated pregnancies and thus suggest the possibility of the use of the markers for the noninvasive prenatal assessment of PET.

Example 4: Placental-Specific PLAC4 mRNA in Maternal Plasma of Trisomy 21 and Normal Pregnancies Determination of Detectability and Pregnancy-Specificity of PLAC4 mRNA The PLAC4 mRNA can be detected in maternal plasma using real-time QRT-PCR assays. In addition, the PLAC4 mRNA was cleared from the maternal plasma following the birth of the child. Thus, the PLAC4 mRNA in maternal plasma is of fetal origin and is pregnancy-specific.

Sample Collection and Processing

Peripheral blood samples from five non-pregnant women, five first-trimester and eight third-trimester pregnant women were collected. Peripheral blood from six third-trimester pregnant women before and at 24 hours after delivery was also obtained. The blood samples were collected in EDTA tubes. Plasma samples were harvested as described in Example 1. RNA extraction from maternal plasma samples was performed following the procedures described in Example 1.

Development of Real-Time QRT-PCR Assay

The QRT-PCR assay for PLAC4 mRNA was developed as described in Example 1. The sequences of the primers (Integrated DNA Technologies, Coralville, Iowa), TaqMan minor groove binding (MGB) fluorescent probes (Applied Biosystems, Foster City, Calif., USA) and the calibrator (Proligo, Singapore) are shown in Table 7.

The QRT-PCR reactions were set up according to the manufacturer's instructions (EZ rTth RNA PCR reagent set, Applied Biosystems) in a reaction volume of 25 µl. The QRT-PCR assays were carried out in an ABI PRISM® 7900HT (Applied Biosystems, Foster City, Calif., USA). The PCR primers and the fluorescent probe were used at concentrations of 400 nM and 100 nM, respectively. 5 µl of extracted RNA were used for amplification. The thermal cycling profile was: the reaction was initiated at 50° C. for 2 min, followed by reverse transcription at 60° C. for 30 min. After a 5-min denaturation at 95° C., 45 cycles of PCR were carried out using denaturation at 95° C. for 15 s and 1 min at 60° C.

PLAC4 mRNA can be Detected in Maternal Plasma and are Pregnancy-Specific

Figure 7:
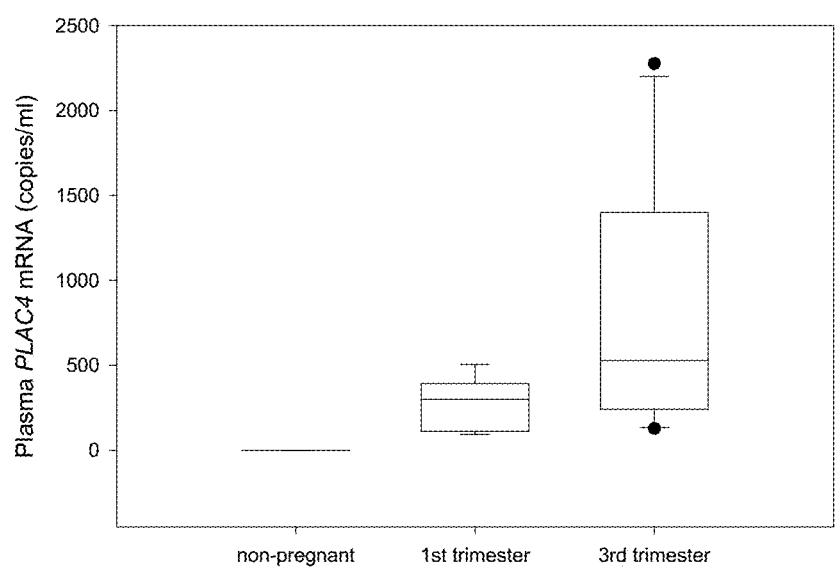
FIG. 7. Box plots of PLAC4 mRNA concentrations in the plasma of non-pregnant women and women in the first and third trimesters of pregnancies. The lines inside the boxes denote the medians. The boxes mark the interval between the $25^{th}$ and $75^{th}$ percentiles. The whiskers denote the interval between the $10^{th}$ and $90^{th}$ percentiles. The filled circles mark the data points outside the $10^{th}$ and $90^{th}$ percentiles.
Figure 8:
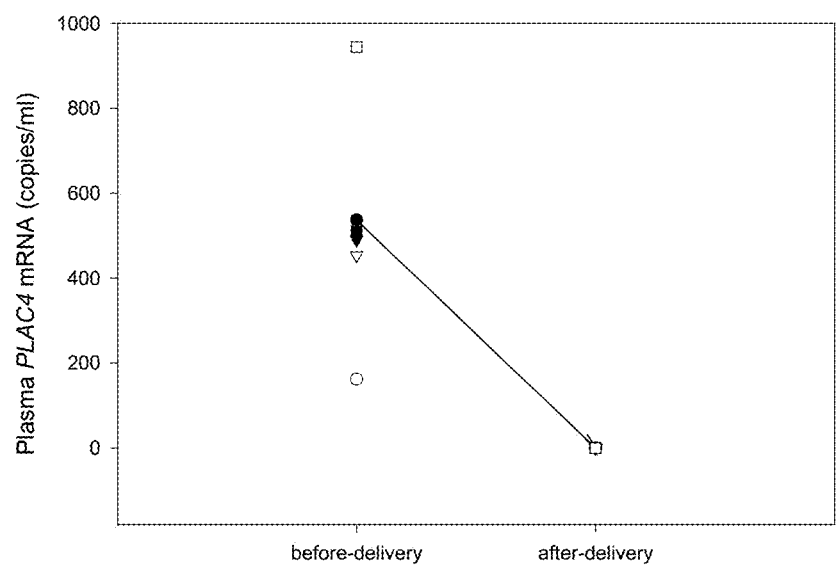
FIG. 8. Clearance of PLAC4 mRNA from maternal plasma after delivery. Each line represents the pair of plasma samples obtained from one subject before and at 24 hours after delivery.
Figure 9A:
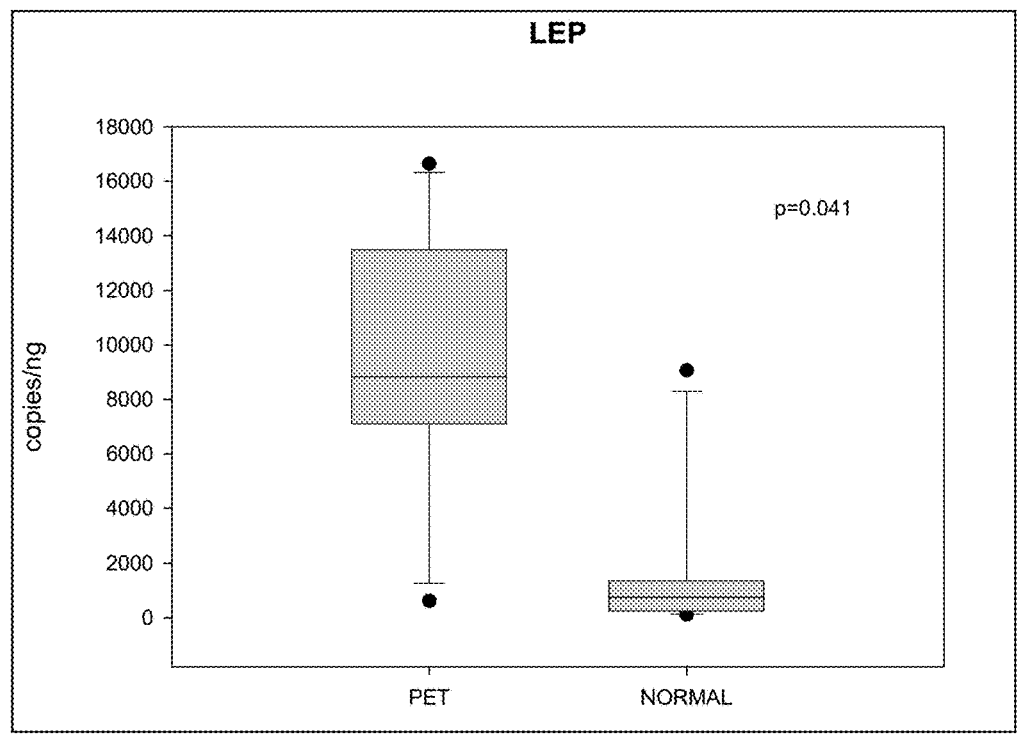
FIG. 9. Comparison of placental tissue levels of RNA transcripts in third-trimester preeclamptic (PET) and control (normal) pregnancies. (A) LEP mRNA. (B) ADAM12 mRNA. (C) PAPPA mRNA. (D) PAPPA2 mRNA. (E) INHBA mRNA. (F) FN1 mRNA. The lines inside the boxes denote the medians. The boxes mark the interval between the 25th and 75th percentiles. The whiskers denote the interval between the 10th and 90th percentiles. The filled circles mark the data points outside the 10th and 90th percentiles.
Figure 9B:
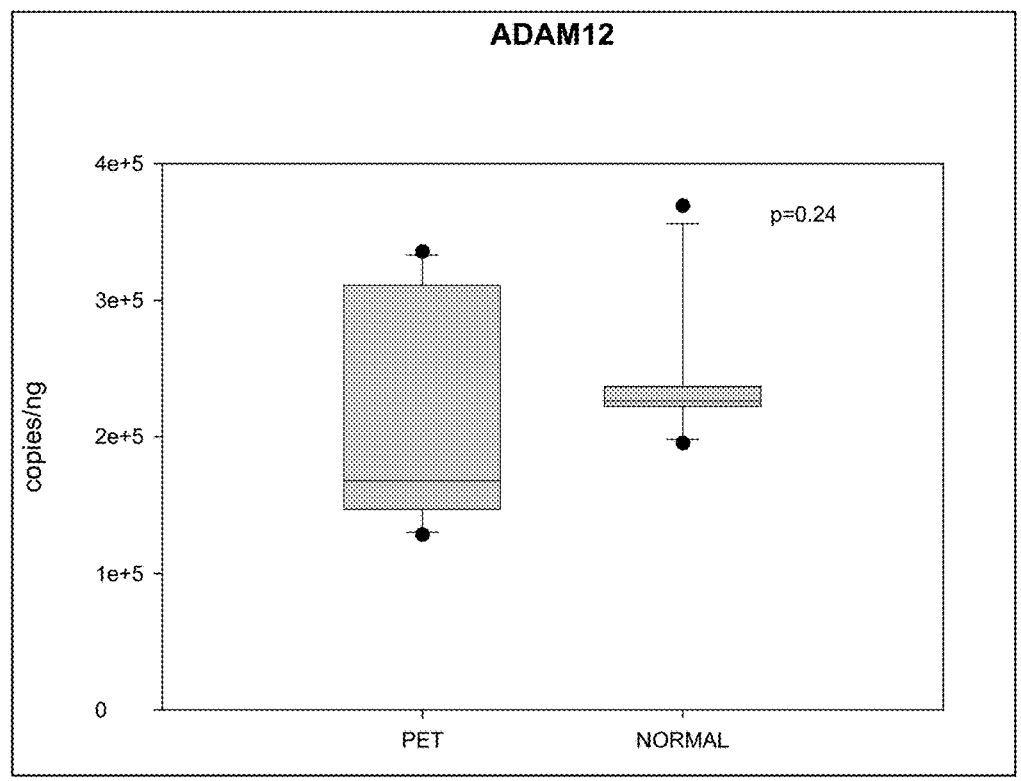
Figure 9C:
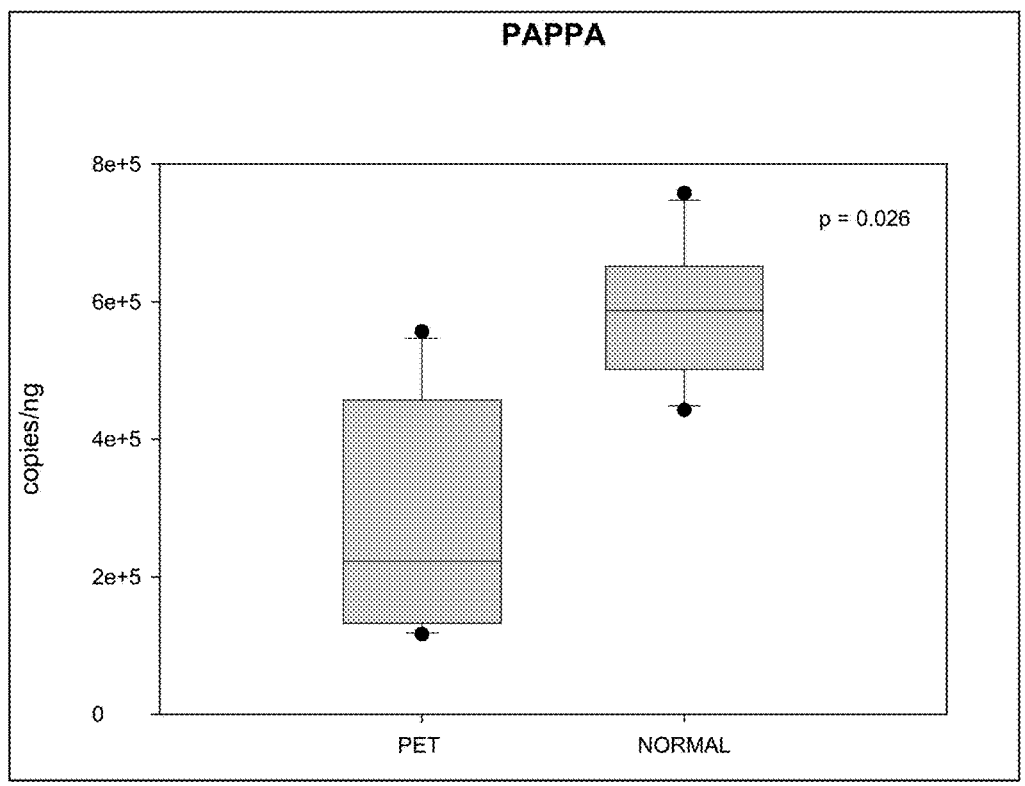
Figure 9D:
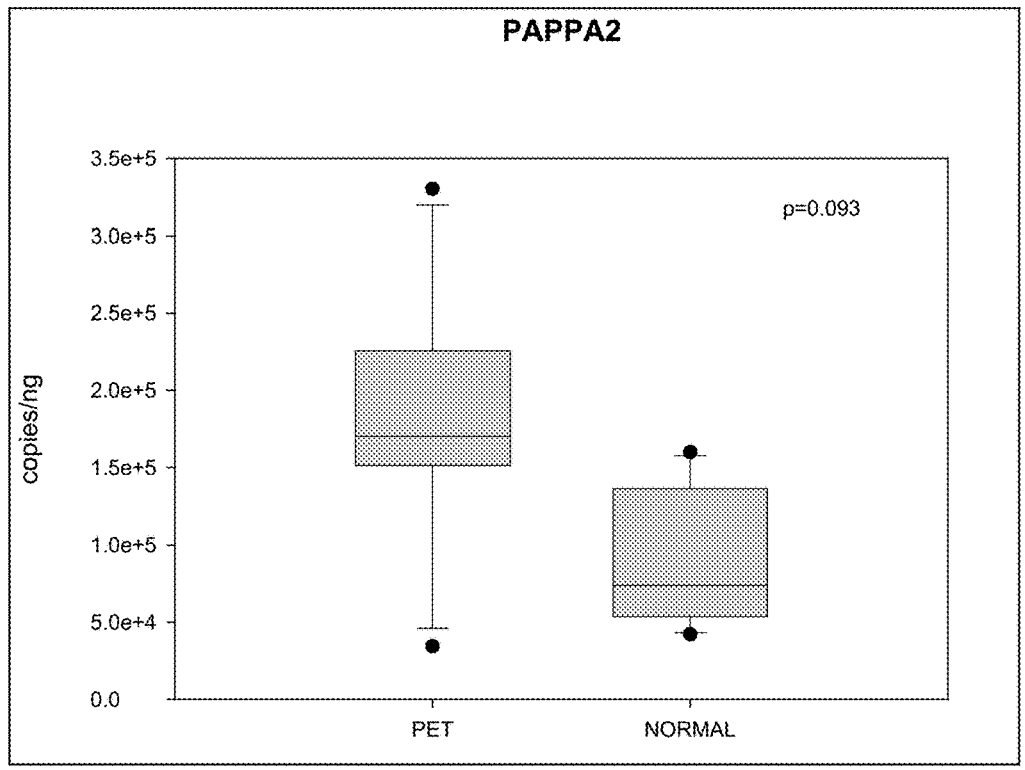
Figure 9E:
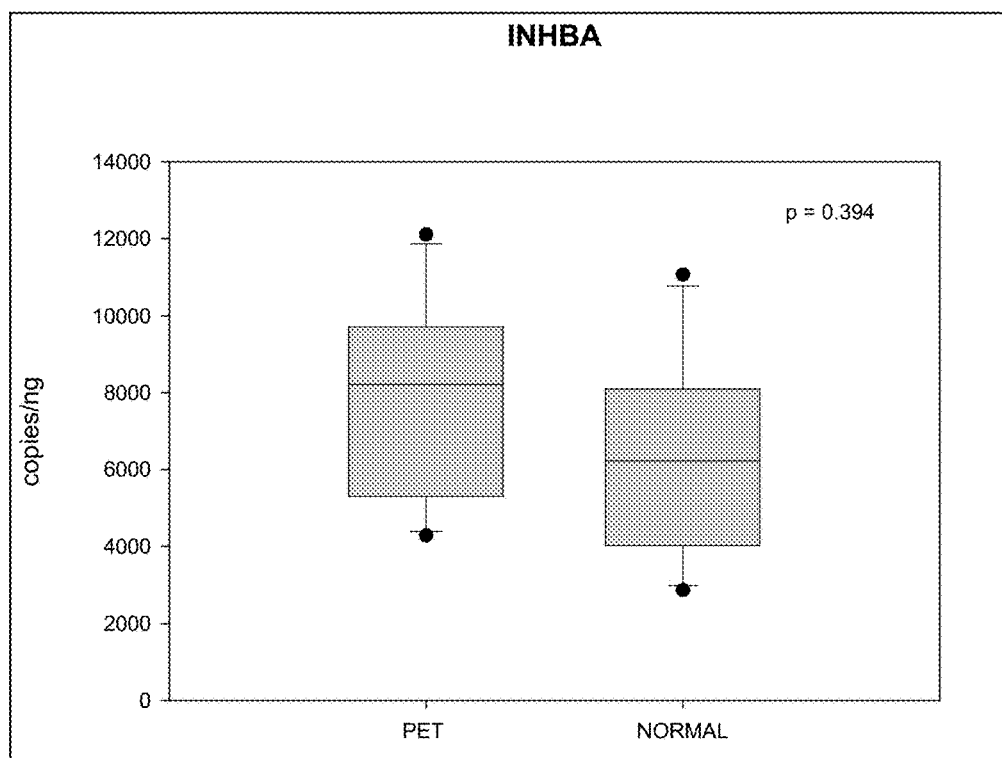
Figure 9F:
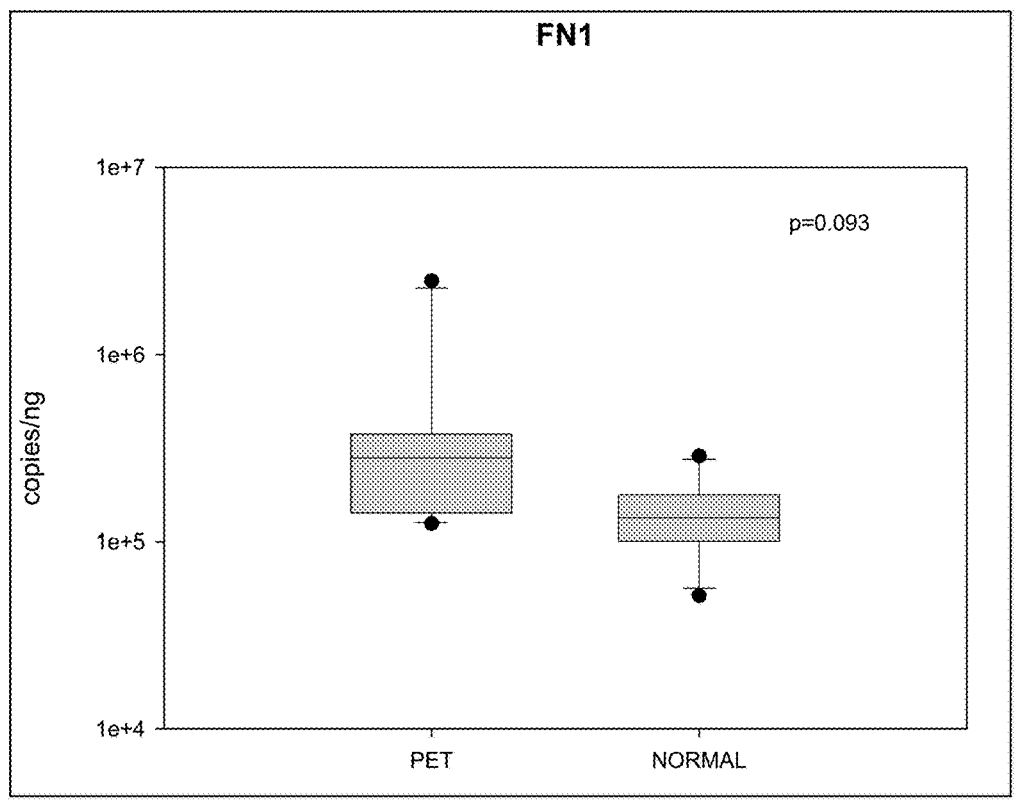

The PLAC4 mRNA could be detected in none of the non-pregnant individuals but all of the first- and third-trimester pregnant women (FIG. 7). The median plasma PLAC4 mRNA concentrations in the first- and third-trimester pregnancies were 299.6 copies/ml and 529.3 copies/ml, respectively. The pregnancy-specificity of the circulating PLAC4 mRNA was also determined. In the pre-delivery plasma samples, the median PLAC4 mRNA concentration was 500.0 copies/ml. The transcript was undetectable in any of the postpartum plasma samples (FIG. 8).

Comparison of Circulating PLAC4 mRNA in Euploid and Trisomy 21 Pregnancies

Circulating PLAC4 mRNA concentrations were compared between karyotypically normal and trisomy 21 pregnancies. Plasma samples were collected from 29 pregnant women carrying euploid fetuses and five pregnant women carrying trisomy 21 fetuses during the first- and second-trimester of pregnancy. The plasma samples were measured for PLAC4 mRNA concentrations by real-time one-step RT-PCR as described. PLAC4 mRNA was detected in all of the trisomic plasma samples. The medians for the trisomy 21 and normal pregnancies are 5581 copies/ml and 4836 copies/ml, respectively. Due to the small sample size, no statistically significant difference was established for the plasma PLAC4 mRNA concentrations between the normal and the trisomy 21 pregnancies.

Example 5: Genes with Aberrant Expression in Placentas of Pregnancies Affected by Preeclampsia Compared with That of Normal Pregnancies Methods
Subjects All placental tissue and blood samples in this study were collected with informed consent from women in the third trimester of pregnancy, who attended the Department of Obstetrics and Gynaecology at the Prince of Wales Hospital, Hong Kong. The study was approved by the Clinical Research Ethics Committee.

In the first part of the study, placental tissue gene expression profiles of both normal and preeclamptic (PET) pregnancies were identified by oligonucleotide microarray. Placental tissues from 5 PET pregnant women (gestational age range: 37-40 weeks) and 5 healthy pregnant women (gestational age range: 38-40 weeks) were obtained immediately after cesarean section. Peripheral blood was collected immediately before delivery. In the second part of the study, the gene expression profiles generated from the oligonucleotide microarray experiments were confirmed using QRT-PCR. Placentas from 6 PET (gestational age range: 30-39 weeks) and 6 healthy pregnant women (gestational age range: 37-39 weeks) were collected immediately after cesarean delivery. Preeclampsia was defined on the basis of a sustained increase in diastolic blood pressure >110 mm Hg on one occasion or >90 mm Hg on two or more occasions at least 4 hours apart, with the presence of significant proteinuria in women with no history of hypertension. Significant proteinuria was defined as proteinuria >0.3 g/day or ≥2+ on dipstick testing in two clean-catch midstream urine specimens collected at least 4 hours apart.

Sample Preparation for Microarray Analysis

Placental tissue samples were stored in RNAlater™ (Ambion®, Austin, Tex.) immediately upon collection and kept at −80° C. until RNA extraction. Six milliliters of maternal peripheral blood were collected concurrently at the time of tissue collection and stored in PAXgene™ Blood RNA Tubes (PreAnalytiX, Hombrechtikon, Switzerland). Total RNA from placental tissues were extracted with Trizol Reagent (Invitrogen, Carlsbad, Calif.) and purified with the RNeasy mini-kit (Qiagen, Hilden, Germany) following manufacturers' protocols. Total RNA from peripheral blood was extracted by the PAXgene™ Blood RNA Kit (PreAnalytiX, Hombrechtikon, Switzerland) according to manufacturer's instructions, with the inclusion of DNase treatment (RNase-Free DNase Set, Qiagen, Hilden, Germany).

Gene Expression Analysis by High Density Oligonucleotide Microarrays

For each sample, ten micrograms of the extracted RNA were labeled and hybridized to the GeneChip® Human Genome U133A and U133B Arrays (Affymetrix, Santa Clara, Calif.) according to the manufacturer's instructions. After hybridization, each array was washed and stained in a GeneChip® Fluidics Station 400 (Affymetrix, Santa Clara, Calif.). The chips were scanned with the GeneArray Scanner (Affymetrix, Santa Clara, Calif.) and analyzed using GeneSpring v 7.2 (Agilent Technologies, Palo Alto, Calif.).

Mining of Microarray Gene Expression Data

The microarray data were imported into GeneSpring v 7.2 (Agilent Technologies) in the .CEL format. Data mining was performed independently for samples (placental tissues and maternal blood cells) collected from the normal and PET pregnancies. Within each group of pregnancies, genes that had relatively higher expression in the placental tissue samples than the maternal blood cells were first identified. Microarray raw data from the 5 placentas and paired maternal blood cells were normalized together using the following steps in sequence: (1) raw data processing by Robust Multichip Average, with GC-content background correction (GC-RMA); (2) data transformation whereby microarray data with values below 0.001 were set to 0.001; and (3) the signal intensity for each gene was divided by the median of its measurements in all samples. Genes with statistically significant (P<0.05) expression in either the placental tissues or maternal blood cells were further identified. These genes were then sorted in the order based on the fold-differences in the placental tissue expression in comparison to that of the maternal blood cells with the aim of identifying transcripts with high fold-differences. This data mining process would lead to the identification of genes with relatively higher expression in placental tissues compared with maternal blood cells.

On the other hand, data mining was performed to identify genes with high absolute expression levels in placental tissues. The raw microarray data for the placental tissues were normalized by GC-RMA processing followed by data transformation whereby microarray data with values below 0.001 were set to 0.001. Genes were then ranked based on the normalized expression levels. Data mining for the placental tissues collected from the normal and preeclamptic pregnancies were performed independently.

Genes were selected for further investigation if they demonstrated much higher fold-differences between the PET placentas in relation to the paired maternal blood than that for the normal pregnancies, or those with much higher absolute expression levels in the PET than the normal placentas while demonstrating at least 200-fold difference between the placental tissue and maternal blood expression.

Real-Time Quantitative RT-PCR

One-step real-time QRT-PCR was used for the quantitative measurement of mRNA transcripts in placental tissues. A calibration curve was prepared by serial dilution of a high performance liquid chromatography-purified single stranded synthetic DNA oligonucleotide with concentrations ranging from $2.5 \times 10^6$ copies to 2.5 copies. Sequences of the primers (Proligo), fluorescent probes (Applied Biosystems, Foster City, Calif., USA) and oligonucleotide calibrators of the studied genes are shown in Table 8.

The QRT-PCR reactions were set up according to the manufacturer's instructions (EZ rTth RNA PCR reagent set, Applied Biosystems) in a reaction volume of 50 µl. The QRT-PCR assays were carried out in a combined thermal cycler and fluorescent detector (ABI Prism 7900HT, Applied Biosystems). For all of the studied transcripts, the fluorescent probes were used at concentrations of 100 nM. 300 nM each of the forward and reverse primers were used for each reaction in the assays for pregnancy-associated plasma protein A, pappalysin 1 (PAPPA), INHBA and FN1. 400 nM each of the forward and reverse primers were used for each reaction in the assays for LEP, ADAM metallopeptidase domain 12 (meltrin alpha) (ADAM12), and pappalysin 2 (PAPPA2). Before performing QRT-PCR, contaminating DNA in the placental tissue RNA extracts was removed by DNase I digestion (Invitrogen, Carlsbad, Calif.) according to the manufacturer's recommendations. 1 ng of extracted placental RNA was used for amplification. Multiple negative water blanks were included in every analysis. Placental tissue RNA concentrations were expressed as copies/ng of placental total RNA.

The thermal profiles used were as follows: the reaction was initiated at 50° C. for 2 min for the included uracil N-glycosylase to act, followed by reverse transcription at 60° C. for 30 min. After a 5-min denaturation at 95° C., 40 cycles of PCR were carried out using denaturation at 92° C. for 15 s and 1 min annealing/extension at 56° C. for LEP, ADAM12, PAPPA and INHBA, but at 57° C. for PAPPA2 and FN1.

Statistical Analysis

Statistical analysis was performed using the Sigma Stat 3.0 software (SPSS).

Results

Genes that were identified from the microarray analysis included LEP, ADAM12 (GenBank Accession No. NM_003474, NM_021641), PAPPA (GenBank Accession No. NM_002581), PAPPA2 (GenBank Accession No. NM_020318, NM_021936), INHBA and FN1. Placental tissue expression levels of the selected transcripts in PET and normal pregnancies were assessed by one-step real-time QRT-PCR. The results are shown in FIG. 9. The concentrations for LEP, ADAM12, PAPPA2, INHBA and FN1 were found to be higher in placental tissues collected from PET than normal pregnancies, while that for PAPPA mRNA was found to be lower in placental tissues collected from PET than normal pregnancies.

Conclusion

Using a microarray-based approach, transcripts with aberrant expression profiles in PET placentas were identified and were considered as potential markers for the investigation of PET. Six transcripts were selected from the microarray analyses and the aberrant nature of their expression profile in PET placentas is confirmed by real-time QRT-PCR.

REFERENCES

Lui, Y Y N, Chik, K W, Chiu, R W K, Ho, C Y, Lam, C W and Lo, Y M D (2002). Predominant hematopoietic origin of cell-free DNA in plasma and serum after sex-mismatched bone marrow transplantation. *Clin Chem* 48, 421-427.

Ng, E K O, Tsui, N B Y, Lam, N Y, Chiu, R W K, Yu, S C, Wong, S C, Lo, E S, Rainer, T H, Johnson, P J and Lo, Y M D (2002). Presence of filterable and nonfilterable mRNA in the plasma of cancer patients and healthy individuals. *Clin Chem* 48, 1212-1217.

Ng, E K O, Tsui, N B Y, Lau, T K, Leung, T N, Chiu, R W K, Panesar, N S, Lit, L C W, Chan, K W and Lo, Y M D (2003). mRNA of placental origin is readily detectable in maternal plasma. *Proc Natl Acad Sci U.S.A.* 100, 4748-4753.

All patents, patent applications, and other publications cited in this application, including published amino acid or polynucleotide sequences, are incorporated by reference in the entirety for all purposes.

TABLE 1A

Sequences of primers and probes for real-time QRT-PCR detection of the placental expressed transcripts encoded on chromosome 21.

| Transcript | | Sequence (SEQ ID NO:) | | |
|---|---|---|---|---|
| COL6A1 | F primer | GACAAAGTCAAGTCCTTCACCAA (1) | Probe | (FAM)CGCTTCATCGACAACC(MGBNFQ) (3) |
| | R primer | GCGTTCCACACCAGGTTT (2) | | |
| COL6A2 | F primer | GATCAACCAGGACACCATCAA (4) | Probe | (FAM)CGCATCATCAAGGTC(MGBNFQ) (6) |
| | R primer | CCGTAGGCTTCGTGTTTCA (5) | | |
| SOD1 | F primer | CAGGGCATCATCAATTTCG (7) | Probe | (FAM)CAGAAGGAAAGTAATGGACCA(MGBNFQ) (9) |
| | R primer | TGCTTCCCCACACCTTCA (8) | | |
| ATP5O | F primer | CCCTCACTACCAACCTGATCA (10) | Probe | (FAM)TGCTTGCTGAAAATG(MGBNFQ) (12) |
| | R primer | CCTTGGGTATTGCTTAATCGA (11) | | |
| BTG3 | F primer | GATGTCCTGAAAGCCTGTGAA (13) | Probe | (FAM)ACAGCTGCATCTTGT(MGBNFQ) (15) |
| | R primer | GGCAAGCCCAGGTCACTA (14) | | |
| APP | F primer | AAGGAAGGCATCCTGCAGTA (16) | Probe | (FAM)TGCCAAGAAGTCTACC(MGBNFQ) (18) |
| | R primer | ACATTGGTGATCTGCAGTTCA (17) | | |
| ATP5J | F primer | CCTGTCCGAATCAGCATGAT (19) | Probe | (FAM)CTTCAGAGGCTCTTCA(MGBNFQ) (21) |
| | R primer | TGACCGAATGACAGAGGAGAA (20) | | |
| ADAMTS1 | F primer | CCACAGGAACTGGAAGCATAA (22) | Probe | (FAM)AAAGAAGCGATTTGTGTCCA(MGBNFQ) (24) |
| | R primer | CAAGCATGGTTTCCACATAGC (23) | | |
| BACE2 | F primer | GGAATGGAATACTTGGCCTAGCT (25) | Probe | (FAM)ATGCCACACTTGCCAAGCCATCAAGTT(TAMRA) (27) |
| | R primer | CACCAGGGAGTCGAAGAAGGT (26) | | |
| DSCR5 | F primer | GAATCTTGGCTAAACTCTTTAGGTTT (28) | Probe | (FAM)ACCTATTGGCCTCAAAAA(MGBNFQ) (30) |
| | R primer | AGGTAATGCAACTGCCCAAT (29) | | |
| ITSN1 | F primer | TGGTGGCAGCCTGGATA (31) | Probe | (FAM)CTGGGCCATAACTG(MGBNFQ) (33) |
| | R primer | ATCATGCTTCGCTCTTTCCT (32) | | |
| PLAC4 | F primer | CCTTTCCCCCTTATCCAACT (34) | Probe | (FAM)CCCTAGCCTATACCC(MGBNFQ) (36) |
| | R primer | GTACTGGTTGGGCTCATTTTCT (35) | | |
| LOC90625 | F primer | TGCACATCGGTCACTGATCT (37) | Probe | (FAM) CCTACTGGCACAGACG(MGFNFQ) (39) |
| | R primer | GGTCAGTTTGGCCGATAAAC (38) | | |
| RPL17 | F primer | TGAGGGTTGACTGGATTGGT (40) | Probe | (FAM)AGGCCCGTGTGGCT(MGBNFQ) (42) |
| | R primer | TACAGCACTGCTTCCACAGAA (41) | | |

MGBNFQ: minor-groove-binding non-fluorescent quencher;
FAM: fluorescent reporter;
TAMRA: fluorescent quencher.

TABLE 1B

Sequences of the oligonucleotide calibrators used in the absolute quantification of the placental expressed transcripts encoded on chromosome 21.

| Transcripts | Calibrator Sequence (SEQ ID NO:) |
|---|---|
| COL6A1 | TGGACAAAGTCAAGTCCTTCACCAAGCGCTTCAT CGACAACCTGAGGGACAGGTACTACCGCTGTGAC CGAAACCTGGTGTGGAACGCAG (43) |
| COL6A2 | GAGATCAACCAGGACACCATCAACCGCATCATCA AGGTCATGAAACACGAAGCCTACGGAG (44) |
| ATP5O | TCCCCTCACTACCAACCTGATCAATTTGCTTGCT GAAAATGGTCGATTAAGCAATACCCAAGGAG (45) |
| SOD1 | TGCAGGGCATCATCAATTTCGAGCAGAAGGAAAG TAATGGACCAGTGAAGGTGTGGGAAGCATT (46) |

TABLE 2A

Microarray detection of placental expressed genes located on Chromosome 21.

| Probe Set ID | GenBank accession no. | Transcripts | Symbol | Location | *Signal (median) |
|---|---|---|---|---|---|
| 213428_s_at | AA292373 | Collagen, type VI, alpha 1 | COL6A1 | 21q22.3 | 8419.2 |
| 200642_at | NM_000454.1 | superoxide dismutase 1, soluble (amyotrophic lateral sclerosis 1 (adult)) | SOD1 | 21q22.11 | 7084.7 |
| 209156_s_at | AY029208.1 | Collagen, type VI, alpha 2 | COL6A2 | 21q22.3 | 7076.9 |
| 200818_at | NM_001697.1 | ATP synthase, H+ transporting, mitochondrial F1 complex, O subunit (oligomycin sensitivity conferring protein) | ATP5O | 21q22.11 | 3247.8 |
| 213134_x_at | AI765445 | BTG family, member 3 | BTG3 | 21q21.1 | 2564.9 |
| 214953_s_at | X06989.1 | amyloid beta (A4) precursor protein (protease nexin-II, Alzheimer disease) | APP | 21q21.3 | 2376.1 |
| 202325_s_at | NM_001685.1 | ATP synthase, H+ transporting, mitochondrial F0 complex, subunit F6 | ATP5J | 21q21.1 | 2303.1 |
| 214750_at | L13197 | placenta-specific 4 | PLAC4 | 21q22.3 | 2209.9 |
| 222162_s_at | AK023795.1 | a disintegrin-like and metalloprotease (reprolysin type) with thrombospondin type 1 motif, 1 | ADAMTS1 | 21q21.2 | 1780.8 |
| 217867_x_at | NM_012105.1 | beta-site APP-cleaving enzyme 2 | BACE2 | 21q22.3 | 1093.4 |
| 221689_s_at | AB035745.1 | Down syndrome critical region gene 5 | DSCR5 | 21q22.2 | 900.7 |
| 209298_s_at | AF114488.1 | intersectin 1 (SH3 domain protein) | ITSN1 | 21q22.1-q22.2 | 199.9 |
| #232191_at | BC005107.1 | hypothetical protein BC005107 | LOC90625 | 21q22.3 | 6910.2 |

*Medians of microarray signals from five first trimester placental tissues
Transcripts that were detected by Human Genome U133B Arrays (Affymetrix). Transcripts without specification were detected by Human Genome U133A Arrays (Affymetrix)

TABLE 2B

Transcript with the highest expression level in first-trimester placentas among the placental expressed genes located on Chromosome 18. The gene was detected by Human Genome U133B Arrays (Affymetrix).

| Probe Set ID | GenBank accession no. | Transcripts | Symbol | Location | *Signal (median) |
|---|---|---|---|---|---|
| 200038_s_at | NM_000985.1 | ribosomal protein L17 | RPL17 | Chr: 18q21 | 25603.6 |

*Medians of microarray signals from five first trimester placental tissues

TABLE 3

Sequences of primers and probes for real-time QRT-PCR detection of the placental expressed transcripts with aberrant expression in trisomy 21.

| Transcript | | Sequence (SEQ ID NO:) | | |
|---|---|---|---|---|
| TFRC | F primer CGGCTGCAGGTTCTTCTG (47) R primer GTTAGAGAATGCTGATCTAGCTTGA (48) | | Probe | (FAM)TGGCAGTTCAGAATGA(MGBNFQ) (49) |
| EFEMP1 | F primer CACAACGTGTGCCAAGACAT (50) R primer CGTAAATTGATGCACACTTGGT (51) | | Probe | (FAM)ACGCACAACTGTAGAGCA(MGBNFQ) (52) |
| ATP5O | F primer CCCTCACTACCAACCTGATCA (53) R primer CCTTGGGTATTGCTTAATCGA (54) | | Probe | (FAM)TGCTTGCTGAAAATG(MGBNFQ) (55) |

MGBNFQ: minor-groove-binding non-fluorescent quencher

TABLE 4

Microarray detection of placental expressed genes with differential expression between trisomy 21 and normal CVS tissues. The genes were detected by Human Genome U133A Arrays (Affymetrix)

| Probe Set ID | GenBank accession no. | Transcript | Symbol | *Signals (Median) | I-count |
|---|---|---|---|---|---|
| 201842_s_at | AI826799 | EGF-containing fibulin-like extracellular matrix protein 1 | EFEMP1 | 11244 | 11 |
| 207332_s_at | NM_003234 | transferrin receptor (p90, CD71) | TFRC | 10645.8 | 11 |
| 200818_at | NM_001697 | ATP synthase, H+ transporting, mitochondrial F1 complex, O subunit (oligomycin sensitivity conferring protein) | ATP5O | 5516.1 | 15 |

*Medians of microarray signals from 3 trisomy 21 CVS

TABLE 5

Sequences of primers and probes for real-time QRT-PCR detection of the preeclampsia-associated placental expressed transcripts.

| Transcript | | | Sequence (SEQ ID NO:) | | | |
|---|---|---|---|---|---|---|
| IGFBP3 | F primer | AGTCCAAGCGGGAGACAG (56) | Probe | (FAM)AATATGGTCCCTGCCG(MGBNFQ) | (58) |
| | R primer | CAGGTGATTCAGTGTGTCTTCC (57) | | | |
| ABP1 | F primer | TGGAAGCAGAGCGAACTG (59) | Probe | (FAM)AGCGAGAGATGCC(MGBNFQ) | (61) |
| | R primer | CATCAGGATGGCAGCCA (60) | | | |
| FN1 | F primer | AAGCAAGCCCGGTTGTTA (62) | Probe | (FAM)ACACTATCAGATAAATCAAC(MGBNFQ) | (64) |
| | R primer | CCAACGCATTGCCTAGGTA (63) | | | |
| INHBA | F primer | CGCCCTCCCAAAGGAT (65) | Probe | (FAM)TACCCAACTCTCAGCCAGAGATGGTG(TAMRA) | (67) |
| | R primer | GCATGTTTAAAATGTGCTTCTTG (66) | | | |
| SLC21A2 | F primer | GCTTTGGGCTCTCCAGTTC (68) | Probe | (FAM) TTTCCAGCTTGAATGAGA (MGBNFQ) | (70) |
| | R primer | GTAGCTGACAAAGATGATGAGGAT (69) | | | |
| SIGLEC6 | F primer | CAAGCTCTCTGTGCGTG (71) | Probe | (FAM) ATGGCCCTGACCCA (MGBNFQ) | (73) |
| | R primer | GTCCCTGGGATGGAGATGT (72) | | | |
| KIAA0992 | F primer | ACCTGTTTGGCTACGAATCC (74) | Probe | (FAM) ACATCTGCTGAGGTGTT (MGBNFQ) | (76) |
| | R primer | GAATCTGTTGAACTGGCACCTT (75) | | | |
| TIMP3 | F primer | CCTTCTGCAACTCCGACAT (77) | Probe | (FAM) CGTGATCCGGGCCA (MGBNFQ) | (79) |
| | R primer | AGCTTCTTCCCCACCACC (78) | | | |
| LEP | F primer | GGTGAGAGCTGCTCTGGAAA (80) | Probe | (FAM)TGACCCAGATCCTC(MGBNFQ) | (82) |
| | R primer | CCTCAGCCTGATTAGGTGGTT (81) | | | |
| LPL | F primer | AGCAAAACCTTCATGGTGATC (83) | Probe | (FAM) TGGCTGGACGGTAAC (MGBNFQ) | (85) |
| | R primer | GCACCCAACTCTCATACATTCC (84) | | | |

MGBNFQ: minor-groove-binding non-fluorescent quencher;
FAM: fluorescent reporter;
TAMRA: fluorescent quencher.

TABLE 6

Microarray detection of placental-expressed genes with differential expression between preeclamptic and normal placental tissues. The genes were detected by Human Genome U133A and U133B Arrays (Affymetrix)

| Probe Set ID | GenBank accession no. | Transcript | Symbol | *PET Signals (Median) | I-count | #SLR (Median) |
|---|---|---|---|---|---|---|
| 210095_s_at | M31159 | insulin-like growth factor binding protein 3 | IGFBP3 | 16136.5 | 16 | 0.5 |
| 203559_s_at | NM_001091 | amiloride binding protein 1 (amine oxidase (copper-containing)) | ABP1 | 13574.5 | 19 | 1.4 |
| 210495_x_at | AF130095 | fibronectin 1 | FN1 | 13005.7 | 13 | 0.4 |
| 210511_s_at | M13436 | inhibin, beta A (activin A, activin AB alpha polypeptide) | INHBA | 10425.5 | 13 | 0.7 |
| 204368_at | NM_005630 | solute carrier family 21 (prostaglandin transporter), member 2 | SLC21A2 | 3800.9 | 15 | 0.6 |

TABLE 6-continued

Microarray detection of placental-expressed genes with differential expression between preeclamptic and normal placental tissues. The genes were detected by Human Genome U133A and U133B Arrays (Affymetrix)

| Probe Set ID | GenBank accession no. | Transcript | Symbol | *PET Signals (Median) | I-count | #SLR (Median) |
|---|---|---|---|---|---|---|
| 210796_x_at | D86359 | sialic acid binding Ig-like lectin 6 | SIGLEC6 | 3731.5 | 16 | 0.8 |
| 200897_s_at | NM_016081 | palladin | KIAA0992 | 3098.5 | 13 | 0.4 |
| 201150_s_at | NM_000362 | tissue inhibitor of metalloproteinase 3 (Sorsby fundus dystrophy, pseudoinflammatory) | TIMP3 | 2979.4 | 13 | 0.4 |
| 207092_at | NM_000230 | leptin (obesity homolog, mouse) | LEP | 2056.6 | 13 | 0.8 |
| 203549_s_at | NM_000237 | lipoprotein lipase | LPL | 1727.0 | 13 | 0.5 |

*Medians of microarray signals from five preeclamptic placental tissues
SLR denotes signal log ratio

TABLE 7

Sequences of the PCR primers, the probe and the calibrator for real-time QRT-PCR detection of PLAC4 mRNA.

| Primer | Sequence (5' to 3') (SEQ ID NO:) |
|---|---|
| F primer | CCTTTCCCCCTTATCCAACT (86) |
| R primer | GTACTGGTTGGGCTCATTTTCT (87) |
| Probe | (FAM) CCCTAGCCTATACCC (MGBNFQ) (88) |
| Calibrator | CACCTTTCCCCCTTATCCAACTAGCCCTAGCCTATACCCTCTGCTGCCCAAGAAAATGAGCCCAACCAGTACAC (89) |

MGBNFQ: minor groove binding non-fluorescent quencher

TABLE 8

Sequences of primers, probes and calibrators for real-time QRT-PCR detection of the preeclampsia-associated placental expressed transcripts.

| Transcript | | Sequence (SEQ ID NO:) | | |
|---|---|---|---|---|
| FN1 | F primer | AAGCAAGCCCGGTTGTTA (90) | Probe | (FAM)ACACTATCAGATAAATCAAC |
| | R primer | CCAACGCATTGCCTAGGTA (91) | | (MGBNFQ) (92) |
| | Calibrator | AAAGCAAGCCCGGTTGTTATGACAATGGAAAACACTATCAGATAAATCAACAGTGGGAGCGGACCTACCTAGGCAATGCGTTGGT (93) | | |
| INHBA | F primer | CGCCCTCCCAAAGGAT (94) | Probe | (FAM)TACCCAACTCTCAGCCAGAGA |
| | R primer | GCATGTTTAAAATGTGCTTCTTG (95) | | TGGTG(TAMRA) (96) |
| | Calibrator | CCGCCCTCCCAAAGGATGTACCCAACTCTCAGCCAGAGATGGTGGAGGCCGTCAAGAAGCACATTTTAAACATGCT (97) | | |
| LEP | F primer | GGTGAGAGCTGCTCTGGAAA (98) | Probe | (FAM)TGACCCAGATCCTC(MGBNFQ) |
| | R primer | CCTCAGCCTGATTAGGTGGTT (99) | | (100) |
| | Calibrator | GGGTGAGAGCTGCTCTGGAAAATGTGACCCAGATCCTCACAACCACCTAATCAGGCTGAGGT (101) | | |
| ADAM12 | F primer | TGGAAAGAAATGAAGGTCTCATTG (102) | Probe | (FAM) CACGGAAACCCACTATCTGCA |
| | R primer | TCGAGCGAGGGAGACATCA (103) | | AGACGGTA(TAMRA)(104) |
| | Calibrator | TGGAAAGAAATGAAGGTCTCATTGCCAGCAGTTTCACGGAAACCCACTATCTGCAAGACGGTACTGATGTCTCCCTCGCTCGAA (105) | | |
| PAPPA2 | F primer | CACAGTGGAAGCCTGGGTTAA (106) | Probe | (FAM) CCGGAGGGAGGACAGAACAAC |
| | R primer | ATCAAACACACCTGCGATGATG (107) | | CCA (TAMRA) (108) |
| | Calibrator | TCACAGTGGAAGCCTGGGTTAAACCGGAGGGAGGACAGAACAACCCAGCCATCATCGCAGGTGTGTTTGATA (109) | | |

TABLE 8-continued

Sequences of primers, probes and calibrators for real-time QRT-PCR detection of the preeclampsia-associated placental expressed transcripts.

| Transcript | | | Sequence (SEQ ID NO:) | | |
|---|---|---|---|---|---|
| PAPPA | F primer | GGGCATTCACACCATCAGT (110) | Probe | FAM-CCAAGACAACAAAGACCCACGCT |
| | R primer | TCGGTCTGTCTTCAAGGAGAA (111) | | ACTT-TAMRA (112) |
| | Calibrator | TGGGCATTCACACCATCAGTGACCAAGACAACAAAGACCCACGCTACTTTTTCTCCTTGAAGA CAGACCGAG (113) | | |

MGBNFQ: minor-groove-binding non-fluorescent quencher;

FAM: fluorescent reporter;

TAMRA: fluorescent quencher.

What is claimed is:

1. A method for detecting the presence of an RNA species in the blood of a pregnant woman, the method comprising the step of:
performing a reverse transcriptase polymerase chain reaction (RT-PCR) to detect the RNA species in a plasma or serum sample obtained from the pregnant woman, wherein the RNA species is derived from RPL17, wherein an oligonucleotide primer comprising SEQ ID NO:40 or SEQ ID NO:41 is used in the RT-PCR.

2. The method of claim 1, wherein step (i) comprises quantitatively determining the amount of the RNA species.

3. The method of claim 2, further comprising step (ii) of comparing the amount of the RNA species from step (i) to a standard control representing the amount of the RNA species in the corresponding sample from an average pregnant woman with a chromosomally normal fetus.

4. The method of claim 3, further comprising step (iii), subsequent to step (ii), of detecting an increase in the amount of the RNA species from the standard control.

5. The method of claim 4, wherein the increase in the amount of mRNA from the standard control is more than 2-fold.

6. The method of claim 1, wherein the plasma or serum sample is obtained from the pregnant woman during the first trimester of gestation.

7. The method of claim 1, wherein the plasma or serum sample is obtained from the pregnant woman during the second or third trimester of gestation.

8. The method of claim 1, wherein the sample is plasma.

9. The method of claim 1, wherein the sample is serum.

* * * * *

SEQUENCE LISTING

<160> NUMBER OF SEQ ID NOS: 113

<210> SEQ ID NO 1
<211> LENGTH: 23
<212> TYPE: DNA
<213> ORGANISM: Artificial Sequence
<220> FEATURE:
<223> OTHER INFORMATION: synthetic QRT-PCR COL6A1 F primer

<400> SEQUENCE: 1
gacaaagtca agtccttcac caa                                           23

<210> SEQ ID NO 2
<211> LENGTH: 18
<212> TYPE: DNA
<213> ORGANISM: Artificial Sequence
<220> FEATURE:
<223> OTHER INFORMATION: synthetic QRT-PCR COL6A1 R primer

<400> SEQUENCE: 2
gcgttccaca ccaggttt                                                 18

<210> SEQ ID NO 3
<211> LENGTH: 16
<212> TYPE: DNA
<213> ORGANISM: Artificial Sequence
<220> FEATURE:
<223> OTHER INFORMATION: synthetic QRT-PCR COL6A1 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (16)...(16)
<223> OTHER INFORMATION: c modified by minor-groove-binding
    non-fluorescent quencher (MGBNFQ)

<400> SEQUENCE: 3
cgcttcatcg acaacc                                                   16

<210> SEQ ID NO 4
<211> LENGTH: 21
<212> TYPE: DNA

<213> ORGANISM: Artificial Sequence
<220> FEATURE:
<223> OTHER INFORMATION: synthetic QRT-PCR COL6A2 F primer

<400> SEQUENCE: 4
gatcaaccag gacaccatca a                                              21

<210> SEQ ID NO 5
<211> LENGTH: 19
<212> TYPE: DNA
<213> ORGANISM: Artificial Sequence
<220> FEATURE:
<223> OTHER INFORMATION: synthetic QRT-PCR COL6A2 R primer

<400> SEQUENCE: 5
ccgtaggctt cgtgtttca                                                 19

<210> SEQ ID NO 6
<211> LENGTH: 15
<212> TYPE: DNA
<213> ORGANISM: Artificial Sequence
<220> FEATURE:
<223> OTHER INFORMATION: synthetic QRT-PCR COL6A2 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (15)...(15)
<223> OTHER INFORMATION: c modified by minor-groove-binding
      non-fluorescent quencher (MGBNFQ)

<400> SEQUENCE: 6
cgcatcatca aggtc                                                     15

<210> SEQ ID NO 7
<211> LENGTH: 19
<212> TYPE: DNA
<213> ORGANISM: Artificial Sequence
<220> FEATURE:
<223> OTHER INFORMATION: synthetic QRT-PCR SOD1 F primer

<400> SEQUENCE: 7
cagggcatca tcaatttcg                                                 19

<210> SEQ ID NO 8
<211> LENGTH: 18
<212> TYPE: DNA
<213> ORGANISM: Artificial Sequence
<220> FEATURE:
<223> OTHER INFORMATION: synthetic QRT-PCR SOD1 R primer

<400> SEQUENCE: 8
tgcttcccca caccttca                                                  18

<210> SEQ ID NO 9
<211> LENGTH: 21
<212> TYPE: DNA
<213> ORGANISM: Artificial Sequence
<220> FEATURE:
<223> OTHER INFORMATION: synthetic QRT-PCR SOD1 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (21)...(21)

```
<223> OTHER INFORMATION: a modified by minor-groove-binding
      non-fluorescent quencher (MGBNFQ)

<400> SEQUENCE: 9
cagaaggaaa gtaatggacc a                                             21

<210> SEQ ID NO 10
<211> LENGTH: 21
<212> TYPE: DNA
<213> ORGANISM: Artificial Sequence
<220> FEATURE:
<223> OTHER INFORMATION: synthetic QRT-PCR ATP5O F primer

<400> SEQUENCE: 10
ccctcactac caacctgatc a                                             21

<210> SEQ ID NO 11
<211> LENGTH: 21
<212> TYPE: DNA
<213> ORGANISM: Artificial Sequence
<220> FEATURE:
<223> OTHER INFORMATION: synthetic QRT-PCR ATP5O R primer

<400> SEQUENCE: 11
ccttgggtat tgcttaatcg a                                             21

<210> SEQ ID NO 12
<211> LENGTH: 15
<212> TYPE: DNA
<213> ORGANISM: Artificial Sequence
<220> FEATURE:
<223> OTHER INFORMATION: synthetic QRT-PCR SOD1 probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (15)...(15)
<223> OTHER INFORMATION: g modified by minor-groove-binding
      non-fluorescent quencher (MGBNFQ)

<400> SEQUENCE: 12
tgcttgctga aaatg                                                    15

<210> SEQ ID NO 13
<211> LENGTH: 21
<212> TYPE: DNA
<213> ORGANISM: Artificial Sequence
<220> FEATURE:
<223> OTHER INFORMATION: synthetic QRT-PCR BTG3 F primer

<400> SEQUENCE: 13
gatgtcctga aagcctgtga a                                             21

<210> SEQ ID NO 14
<211> LENGTH: 18
<212> TYPE: DNA
<213> ORGANISM: Artificial Sequence
<220> FEATURE:
<223> OTHER INFORMATION: synthetic QRT-PCR BTG3 R primer

<400> SEQUENCE: 14
ggcaagccca ggtcacta                                                 18

<210> SEQ ID NO 15
<211> LENGTH: 15
```

```
<212> TYPE: DNA
<213> ORGANISM: Artificial Sequence
<220> FEATURE:
<223> OTHER INFORMATION: synthetic QRT-PCR BTG3 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (15)...(15)
<223> OTHER INFORMATION: t modified by minor-groove-binding
      non-fluorescent quencher (MGBNFQ)

<400> SEQUENCE: 15
acagctgcat cttgt                                                       15

<210> SEQ ID NO 16
<211> LENGTH: 20
<212> TYPE: DNA
<213> ORGANISM: Artificial Sequence
<220> FEATURE:
<223> OTHER INFORMATION: synthetic QRT-PCR APP F primer

<400> SEQUENCE: 16
aaggaaggca tcctgcagta                                                  20

<210> SEQ ID NO 17
<211> LENGTH: 21
<212> TYPE: DNA
<213> ORGANISM: Artificial Sequence
<220> FEATURE:
<223> OTHER INFORMATION: synthetic QRT-PCR APP R primer

<400> SEQUENCE: 17
acattggtga tctgcagttc a                                                21

<210> SEQ ID NO 18
<211> LENGTH: 16
<212> TYPE: DNA
<213> ORGANISM: Artificial Sequence
<220> FEATURE:
<223> OTHER INFORMATION: synthetic QRT-PCR APP probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (16)...(16)
<223> OTHER INFORMATION: c modified by minor-groove-binding
      non-fluorescent quencher (MGBNFQ)

<400> SEQUENCE: 18
tgccaagaag tctacc                                                      16

<210> SEQ ID NO 19
<211> LENGTH: 20
<212> TYPE: DNA
<213> ORGANISM: Artificial Sequence
<220> FEATURE:
<223> OTHER INFORMATION: synthetic QRT-PCR ATP5J F primer

<400> SEQUENCE: 19
cctgtccgaa tcagcatgat                                                  20

<210> SEQ ID NO 20
<211> LENGTH: 21
<212> TYPE: DNA
```

```
<213> ORGANISM: Artificial Sequence
<220> FEATURE:
<223> OTHER INFORMATION: synthetic QRT-PCR ATP5J R primer

<400> SEQUENCE: 20
tgaccgaatg acagaggaga a                                              21

<210> SEQ ID NO 21
<211> LENGTH: 16
<212> TYPE: DNA
<213> ORGANISM: Artificial Sequence
<220> FEATURE:
<223> OTHER INFORMATION: synthetic QRT-PCR ATP5J probe
<220> FEATURE:
<221> NAME/KEY: modified_base
<222> LOCATION: (1)...(1)
<223> OTHER INFORMATION: c modified by FAM fluorescent
<220> FEATURE:
<221> NAME/KEY: modified_base
<222> LOCATION: (16)...(16)
<223> OTHER INFORMATION: a modified by minor-groove-binding
      non-fluorescent quencher (MGBNFQ)

<400> SEQUENCE: 21
cttcagaggc tcttca                                                    16

<210> SEQ ID NO 22
<211> LENGTH: 21
<212> TYPE: DNA
<213> ORGANISM: Artificial Sequence
<220> FEATURE:
<223> OTHER INFORMATION: synthetic QRT-PCR ADAMTS1 F primer

<400> SEQUENCE: 22
ccacaggaac tggaagcata a                                              21

<210> SEQ ID NO 23
<211> LENGTH: 21
<212> TYPE: DNA
<213> ORGANISM: Artificial Sequence
<220> FEATURE:
<223> OTHER INFORMATION: synthetic QRT-PCR ADAMTS1 R primer

<400> SEQUENCE: 23
caagcatggt ttccacatag c                                              21

<210> SEQ ID NO 24
<211> LENGTH: 20
<212> TYPE: DNA
<213> ORGANISM: Artificial Sequence
<220> FEATURE:
<223> OTHER INFORMATION: synthetic QRT-PCR ADAMT1 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (20)...(20)
<223> OTHER INFORMATION: a modified by minor-groove-binding
      non-fluorescent quencher (MGBNFQ)

<400> SEQUENCE: 24
aaagaagcga tttgtgtcca                                                20

<210> SEQ ID NO 25
<211> LENGTH: 23
<212> TYPE: DNA
<213> ORGANISM: Artificial Sequence
```

```
<220> FEATURE:
<223> OTHER INFORMATION: synthetic QRT-PCR BACE2 F primer

<400> SEQUENCE: 25
ggaatggaat acttggccta gct                                             23

<210> SEQ ID NO 26
<211> LENGTH: 21
<212> TYPE: DNA
<213> ORGANISM: Artificial Sequence
<220> FEATURE:
<223> OTHER INFORMATION: synthetic QRT-PCR BACE2 R primer

<400> SEQUENCE: 26
caccagggag tcgaagaagg t                                               21

<210> SEQ ID NO 27
<211> LENGTH: 27
<212> TYPE: DNA
<213> ORGANISM: Artificial Sequence
<220> FEATURE:
<223> OTHER INFORMATION: synthetic QRT-PCR BACE2 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (27)...(27)
<223> OTHER INFORMATION: t modified by TAMRA fluorescent quencher

<400> SEQUENCE: 27
atgccacact tgccaagcca tcaagtt                                         27

<210> SEQ ID NO 28
<211> LENGTH: 26
<212> TYPE: DNA
<213> ORGANISM: Artificial Sequence
<220> FEATURE:
<223> OTHER INFORMATION: synthetic QRT-PCR DSCR5 F primer

<400> SEQUENCE: 28
gaatcttggc taaactcttt aggttt                                          26

<210> SEQ ID NO 29
<211> LENGTH: 20
<212> TYPE: DNA
<213> ORGANISM: Artificial Sequence
<220> FEATURE:
<223> OTHER INFORMATION: synthetic QRT-PCR DSCR5 R primer

<400> SEQUENCE: 29
aggtaatgca actgcccaat                                                 20

<210> SEQ ID NO 30
<211> LENGTH: 18
<212> TYPE: DNA
<213> ORGANISM: Artificial Sequence
<220> FEATURE:
<223> OTHER INFORMATION: synthetic QRT-PCR DSCR5 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (18)...(18)
<223> OTHER INFORMATION: a modified by minor-groove-binding
      non-fluorescent quencher (MGBNFQ)
```

-continued

```
<400> SEQUENCE: 30
acctattggc ctcaaaaa                                                  18

<210> SEQ ID NO 31
<211> LENGTH: 17
<212> TYPE: DNA
<213> ORGANISM: Artificial Sequence
<220> FEATURE:
<223> OTHER INFORMATION: synthetic QRT-PCR ITSN1 F primer

<400> SEQUENCE: 31
tggtggcagc ctggata                                                   17

<210> SEQ ID NO 32
<211> LENGTH: 20
<212> TYPE: DNA
<213> ORGANISM: Artificial Sequence
<220> FEATURE:
<223> OTHER INFORMATION: synthetic QRT-PCR ITSN1 R primer

<400> SEQUENCE: 32
atcatgcttc gctctttcct                                                20

<210> SEQ ID NO 33
<211> LENGTH: 14
<212> TYPE: DNA
<213> ORGANISM: Artificial Sequence
<220> FEATURE:
<223> OTHER INFORMATION: synthetic QRT-PCR ITSN1 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (14)...(14)
<223> OTHER INFORMATION: g modified by minor-groove-binding
      non-fluorescent quencher (MGBNFQ)

<400> SEQUENCE: 33
ctgggccata actg                                                      14

<210> SEQ ID NO 34
<211> LENGTH: 20
<212> TYPE: DNA
<213> ORGANISM: Artificial Sequence
<220> FEATURE:
<223> OTHER INFORMATION: synthetic QRT-PCR PLAC4 F primer

<400> SEQUENCE: 34
cctttccccc ttatccaact                                                20

<210> SEQ ID NO 35
<211> LENGTH: 22
<212> TYPE: DNA
<213> ORGANISM: Artificial Sequence
<220> FEATURE:
<223> OTHER INFORMATION: synthetic QRT-PCR PLAC4 R primer

<400> SEQUENCE: 35
gtactggttg ggctcatttt ct                                             22

<210> SEQ ID NO 36
<211> LENGTH: 15
<212> TYPE: DNA
<213> ORGANISM: Artificial Sequence
```

```
<220> FEATURE:
<223> OTHER INFORMATION: synthetic QRT-PCR PLAC4 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (15)...(15)
<223> OTHER INFORMATION: c modified by minor-groove-binding
      non-fluorescent quencher (MGBNFQ)

<400> SEQUENCE: 36
ccctagccta taccc                                                    15

<210> SEQ ID NO 37
<211> LENGTH: 20
<212> TYPE: DNA
<213> ORGANISM: Artificial Sequence
<220> FEATURE:
<223> OTHER INFORMATION: synthetic QRT-PCR LOC90625 F primer

<400> SEQUENCE: 37
tgcacatcgg tcactgatct                                               20

<210> SEQ ID NO 38
<211> LENGTH: 20
<212> TYPE: DNA
<213> ORGANISM: Artificial Sequence
<220> FEATURE:
<223> OTHER INFORMATION: synthetic QRT-PCR LOC90625 R primer

<400> SEQUENCE: 38
ggtcagtttg gccgataaac                                               20

<210> SEQ ID NO 39
<211> LENGTH: 16
<212> TYPE: DNA
<213> ORGANISM: Artificial Sequence
<220> FEATURE:
<223> OTHER INFORMATION: synthetic QRT-PCR LOC90625 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (16)...(16)
<223> OTHER INFORMATION: g modified by minor-groove-binding
      non-fluorescent quencher (MGBNFQ)

<400> SEQUENCE: 39
cctactggca cagacg                                                   16

<210> SEQ ID NO 40
<211> LENGTH: 20
<212> TYPE: DNA
<213> ORGANISM: Artificial Sequence
<220> FEATURE:
<223> OTHER INFORMATION: synthetic QRT-PCR RPL17 F primer

<400> SEQUENCE: 40
tgagggttga ctggattggt                                               20

<210> SEQ ID NO 41
<211> LENGTH: 21
<212> TYPE: DNA
<213> ORGANISM: Artificial Sequence
<220> FEATURE:
```

<223> OTHER INFORMATION: synthetic QRT-PCR RPL17 R primer

<400> SEQUENCE: 41
tacagcactg cttccacaga a    21

<210> SEQ ID NO 42
<211> LENGTH: 14
<212> TYPE: DNA
<213> ORGANISM: Artificial Sequence
<220> FEATURE:
<223> OTHER INFORMATION: synthetic QRT-PCR RPL17 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (14)...(14)
<223> OTHER INFORMATION: t modified by minor-groove-binding
    non-fluorescent quencher (MGBNFQ)

<400> SEQUENCE: 42
aggcccgtgt ggct    14

<210> SEQ ID NO 43
<211> LENGTH: 90
<212> TYPE: DNA
<213> ORGANISM: Artificial Sequence
<220> FEATURE:
<223> OTHER INFORMATION: synthetic QRT-PCR COL6A1 oligonucleotide
    calibrator sequence

<400> SEQUENCE: 43
tggacaaagt caagtccttc accaagcgct tcatcgacaa cctgagggac aggtactacc    60
gctgtgaccg aaacctggtg tggaacgcag    90

<210> SEQ ID NO 44
<211> LENGTH: 61
<212> TYPE: DNA
<213> ORGANISM: Artificial Sequence
<220> FEATURE:
<223> OTHER INFORMATION: synthetic QRT-PCR COL6A2 oligonucleotide
    calibrator sequence

<400> SEQUENCE: 44
gagatcaacc aggacaccat caaccgcatc atcaaggtca tgaaacacga agcctacgga    60
g    61

<210> SEQ ID NO 45
<211> LENGTH: 65
<212> TYPE: DNA
<213> ORGANISM: Artificial Sequence
<220> FEATURE:
<223> OTHER INFORMATION: synthetic QRT-PCR ATP5O oligonucleotide
    calibrator sequence

<400> SEQUENCE: 45
tcccctcact accaacctga tcaatttgct tgctgaaaat ggtcgattaa gcaataccca    60
aggag    65

<210> SEQ ID NO 46
<211> LENGTH: 65
<212> TYPE: DNA
<213> ORGANISM: Artificial Sequence
<220> FEATURE:
<223> OTHER INFORMATION: synthetic QRT-PCR SOD1 oligonucleotide calibrator sequence

<400> SEQUENCE: 46
tgcagggcat catcaatttc gagcagaagg aaagtaatgg accagtgaag gtgtggggaa    60
gcatt                                                               65

<210> SEQ ID NO 47
<211> LENGTH: 18
<212> TYPE: DNA
<213> ORGANISM: Artificial Sequence
<220> FEATURE:
<223> OTHER INFORMATION: synthetic QRT-PCR TFRC F primer

<400> SEQUENCE: 47
cggctgcagg ttcttctg                                                 18

<210> SEQ ID NO 48
<211> LENGTH: 25
<212> TYPE: DNA
<213> ORGANISM: Artificial Sequence
<220> FEATURE:
<223> OTHER INFORMATION: synthetic QRT-PCR TFRC R primer

<400> SEQUENCE: 48
gttagagaat gctgatctag cttga                                         25

<210> SEQ ID NO 49
<211> LENGTH: 16
<212> TYPE: DNA
<213> ORGANISM: Artificial Sequence
<220> FEATURE:
<223> OTHER INFORMATION: synthetic QRT-PCR TFRC probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (16)...(16)
<223> OTHER INFORMATION: a modified by minor-groove-binding
    non-fluorescent quencher (MGBNFQ)

<400> SEQUENCE: 49
tggcagttca gaatga                                                   16

<210> SEQ ID NO 50
<211> LENGTH: 20
<212> TYPE: DNA
<213> ORGANISM: Artificial Sequence
<220> FEATURE:
<223> OTHER INFORMATION: synthetic QRT-PCR EFEMP1 F primer

<400> SEQUENCE: 50
cacaacgtgt gccaagacat                                               20

<210> SEQ ID NO 51
<211> LENGTH: 22
<212> TYPE: DNA
<213> ORGANISM: Artificial Sequence
<220> FEATURE:
<223> OTHER INFORMATION: synthetic QRT-PCR EFEMP1 R primer

<400> SEQUENCE: 51
cgtaaattga tgcacacttg gt                                            22

<210> SEQ ID NO 52

```
<211> LENGTH: 18
<212> TYPE: DNA
<213> ORGANISM: Artificial Sequence
<220> FEATURE:
<223> OTHER INFORMATION: synthetic QRT-PCR EFEMP1 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (18)...(18)
<223> OTHER INFORMATION: a modified by minor-groove-binding
      non-fluorescent quencher (MGBNFQ)

<400> SEQUENCE: 52
acgcacaact gtagagca                                                       18

<210> SEQ ID NO 53
<211> LENGTH: 21
<212> TYPE: DNA
<213> ORGANISM: Artificial Sequence
<220> FEATURE:
<223> OTHER INFORMATION: synthetic QRT-PCR ATP5O F primer

<400> SEQUENCE: 53
ccctcactac caacctgatc a                                                   21

<210> SEQ ID NO 54
<211> LENGTH: 21
<212> TYPE: DNA
<213> ORGANISM: Artificial Sequence
<220> FEATURE:
<223> OTHER INFORMATION: synthetic QRT-PCR ATP5O R primer

<400> SEQUENCE: 54
ccttgggtat tgcttaatcg a                                                   21

<210> SEQ ID NO 55
<211> LENGTH: 15
<212> TYPE: DNA
<213> ORGANISM: Artificial Sequence
<220> FEATURE:
<223> OTHER INFORMATION: synthetic QRT-PCR ATP5O probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (15)...(15)
<223> OTHER INFORMATION: g modified by minor-groove-binding
      non-fluorescent quencher (MGBNFQ)

<400> SEQUENCE: 55
tgcttgctga aaatg                                                          15

<210> SEQ ID NO 56
<211> LENGTH: 18
<212> TYPE: DNA
<213> ORGANISM: Artificial Sequence
<220> FEATURE:
<223> OTHER INFORMATION: synthetic QRT-PCR IGFBP3 F primer

<400> SEQUENCE: 56
agtccaagcg ggagacag                                                       18

<210> SEQ ID NO 57
<211> LENGTH: 22
```

```
<212> TYPE: DNA
<213> ORGANISM: Artificial Sequence
<220> FEATURE:
<223> OTHER INFORMATION: synthetic QRT-PCR IGFBP3 R primer

<400> SEQUENCE: 57
caggtgattc agtgtgtctt cc                                              22

<210> SEQ ID NO 58
<211> LENGTH: 16
<212> TYPE: DNA
<213> ORGANISM: Artificial Sequence
<220> FEATURE:
<223> OTHER INFORMATION: synthetic QRT-PCR IGFBP3 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (16)...(16)
<223> OTHER INFORMATION: g modified by minor-groove-binding
      non-fluorescent quencher (MGBNFQ)

<400> SEQUENCE: 58
aatatggtcc ctgccg                                                     16

<210> SEQ ID NO 59
<211> LENGTH: 18
<212> TYPE: DNA
<213> ORGANISM: Artificial Sequence
<220> FEATURE:
<223> OTHER INFORMATION: synthetic QRT-PCR ABP1 F primer

<400> SEQUENCE: 59
tggaagcaga gcgaactg                                                   18

<210> SEQ ID NO 60
<211> LENGTH: 17
<212> TYPE: DNA
<213> ORGANISM: Artificial Sequence
<220> FEATURE:
<223> OTHER INFORMATION: synthetic QRT-PCR ABP1 R primer

<400> SEQUENCE: 60
catcaggatg gcagcca                                                    17

<210> SEQ ID NO 61
<211> LENGTH: 13
<212> TYPE: DNA
<213> ORGANISM: Artificial Sequence
<220> FEATURE:
<223> OTHER INFORMATION: synthetic QRT-PCR ABP1 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (13)...(13)
<223> OTHER INFORMATION: c modified by minor-groove-binding
      non-fluorescent quencher (MGBNFQ)

<400> SEQUENCE: 61
agcgagagat gcc                                                        13

<210> SEQ ID NO 62
<211> LENGTH: 18
<212> TYPE: DNA
```

```
<213> ORGANISM: Artificial Sequence
<220> FEATURE:
<223> OTHER INFORMATION: synthetic QRT-PCR FN1 F primer

<400> SEQUENCE: 62
aagcaagccc ggttgtta                                                  18

<210> SEQ ID NO 63
<211> LENGTH: 19
<212> TYPE: DNA
<213> ORGANISM: Artificial Sequence
<220> FEATURE:
<223> OTHER INFORMATION: synthetic QRT-PCR FN1 R primer

<400> SEQUENCE: 63
ccaacgcatt gcctaggta                                                 19

<210> SEQ ID NO 64
<211> LENGTH: 20
<212> TYPE: DNA
<213> ORGANISM: Artificial Sequence
<220> FEATURE:
<223> OTHER INFORMATION: synthetic QRT-PCR FN1 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (20)...(20)
<223> OTHER INFORMATION: c modified by minor-groove-binding
      non-fluorescent quencher (MGBNFQ)

<400> SEQUENCE: 64
acactatcag ataaatcaac                                                20

<210> SEQ ID NO 65
<211> LENGTH: 16
<212> TYPE: DNA
<213> ORGANISM: Artificial Sequence
<220> FEATURE:
<223> OTHER INFORMATION: synthetic QRT-PCR INHBA F primer

<400> SEQUENCE: 65
cgccctccca aaggat                                                    16

<210> SEQ ID NO 66
<211> LENGTH: 23
<212> TYPE: DNA
<213> ORGANISM: Artificial Sequence
<220> FEATURE:
<223> OTHER INFORMATION: synthetic QRT-PCR INHBA R primer

<400> SEQUENCE: 66
gcatgtttaa aatgtgcttc ttg                                            23

<210> SEQ ID NO 67
<211> LENGTH: 26
<212> TYPE: DNA
<213> ORGANISM: Artificial Sequence
<220> FEATURE:
<223> OTHER INFORMATION: synthetic QRT-PCR INHBA probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (26)...(26)
```

<223> OTHER INFORMATION: g modified by TAMRA fluorescent quencher

<400> SEQUENCE: 67
tacccaactc tcagccagag atggtg                                        26

<210> SEQ ID NO 68
<211> LENGTH: 19
<212> TYPE: DNA
<213> ORGANISM: Artificial Sequence
<220> FEATURE:
<223> OTHER INFORMATION: synthetic QRT-PCR SLC21A2 F primer

<400> SEQUENCE: 68
gctttgggct ctccagttc                                                19

<210> SEQ ID NO 69
<211> LENGTH: 24
<212> TYPE: DNA
<213> ORGANISM: Artificial Sequence
<220> FEATURE:
<223> OTHER INFORMATION: synthetic QRT-PCR SLC21A2 R primer

<400> SEQUENCE: 69
gtagctgaca aagatgatga ggat                                          24

<210> SEQ ID NO 70
<211> LENGTH: 18
<212> TYPE: DNA
<213> ORGANISM: Artificial Sequence
<220> FEATURE:
<223> OTHER INFORMATION: synthetic QRT-PCR SLC21A2 probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (18)...(18)
<223> OTHER INFORMATION: a modified by minor-groove-binding
      non-fluorescent quencher (MGBNFQ)

<400> SEQUENCE: 70
tttccagctt gaatgaga                                                 18

<210> SEQ ID NO 71
<211> LENGTH: 17
<212> TYPE: DNA
<213> ORGANISM: Artificial Sequence
<220> FEATURE:
<223> OTHER INFORMATION: synthetic QRT-PCR SIGLEC6 F primer

<400> SEQUENCE: 71
caagctctct gtgcgtg                                                  17

<210> SEQ ID NO 72
<211> LENGTH: 19
<212> TYPE: DNA
<213> ORGANISM: Artificial Sequence
<220> FEATURE:
<223> OTHER INFORMATION: synthetic QRT-PCR SIGLEC6 R primer

<400> SEQUENCE: 72
gtccctggga tggagatgt                                                19

<210> SEQ ID NO 73
<211> LENGTH: 14
<212> TYPE: DNA

```
<213> ORGANISM: Artificial Sequence
<220> FEATURE:
<223> OTHER INFORMATION: synthetic QRT-PCR SIGLEC6 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (14)...(14)
<223> OTHER INFORMATION: a modified by minor-groove-binding
      non-fluorescent quencher (MGBNFQ)

<400> SEQUENCE: 73
atggccctga ccca                                                         14

<210> SEQ ID NO 74
<211> LENGTH: 20
<212> TYPE: DNA
<213> ORGANISM: Artificial Sequence
<220> FEATURE:
<223> OTHER INFORMATION: synthetic QRT-PCR KIAA0992 F primer

<400> SEQUENCE: 74
acctgtttgg ctacgaatcc                                                   20

<210> SEQ ID NO 75
<211> LENGTH: 22
<212> TYPE: DNA
<213> ORGANISM: Artificial Sequence
<220> FEATURE:
<223> OTHER INFORMATION: synthetic QRT-PCR KIAA0992 R primer

<400> SEQUENCE: 75
gaatctgttg aactggcacc tt                                                22

<210> SEQ ID NO 76
<211> LENGTH: 17
<212> TYPE: DNA
<213> ORGANISM: Artificial Sequence
<220> FEATURE:
<223> OTHER INFORMATION: synthetic QRT-PCR KIAA0992 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (17)...(17)
<223> OTHER INFORMATION: t modified by minor-groove-binding
      non-fluorescent quencher (MGBNFQ)

<400> SEQUENCE: 76
acatctgctg aggtgtt                                                      17

<210> SEQ ID NO 77
<211> LENGTH: 19
<212> TYPE: DNA
<213> ORGANISM: Artificial Sequence
<220> FEATURE:
<223> OTHER INFORMATION: synthetic QRT-PCR TIMP3 F primer

<400> SEQUENCE: 77
ccttctgcaa ctccgacat                                                    19

<210> SEQ ID NO 78
<211> LENGTH: 18
<212> TYPE: DNA
<213> ORGANISM: Artificial Sequence
```

<220> FEATURE:
<223> OTHER INFORMATION: synthetic QRT-PCR TIMP3 R primer

<400> SEQUENCE: 78
agcttcttcc ccaccacc                                                   18

<210> SEQ ID NO 79
<211> LENGTH: 14
<212> TYPE: DNA
<213> ORGANISM: Artificial Sequence
<220> FEATURE:
<223> OTHER INFORMATION: synthetic QRT-PCR TIMP3 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (14)...(14)
<223> OTHER INFORMATION: a modified by minor-groove-binding
      non-fluorescent quencher (MGBNFQ)

<400> SEQUENCE: 79
cgtgatccgg gcca                                                       14

<210> SEQ ID NO 80
<211> LENGTH: 20
<212> TYPE: DNA
<213> ORGANISM: Artificial Sequence
<220> FEATURE:
<223> OTHER INFORMATION: synthetic QRT-PCR LEP F primer

<400> SEQUENCE: 80
ggtgagagct gctctggaaa                                                 20

<210> SEQ ID NO 81
<211> LENGTH: 21
<212> TYPE: DNA
<213> ORGANISM: Artificial Sequence
<220> FEATURE:
<223> OTHER INFORMATION: synthetic QRT-PCR LEP R primer

<400> SEQUENCE: 81
cctcagcctg attaggtggt t                                               21

<210> SEQ ID NO 82
<211> LENGTH: 14
<212> TYPE: DNA
<213> ORGANISM: Artificial Sequence
<220> FEATURE:
<223> OTHER INFORMATION: synthetic QRT-PCR LEP probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (14)...(14)
<223> OTHER INFORMATION: c modified by minor-groove-binding
      non-fluorescent quencher (MGBNFQ)

<400> SEQUENCE: 82
tgacccagat cctc                                                       14

<210> SEQ ID NO 83
<211> LENGTH: 21
<212> TYPE: DNA
<213> ORGANISM: Artificial Sequence
<220> FEATURE:

<223> OTHER INFORMATION: synthetic QRT-PCR LPL F primer

<400> SEQUENCE: 83
agcaaaacct tcatggtgat c                                    21

<210> SEQ ID NO 84
<211> LENGTH: 22
<212> TYPE: DNA
<213> ORGANISM: Artificial Sequence
<220> FEATURE:
<223> OTHER INFORMATION: synthetic QRT-PCR LPL R primer

<400> SEQUENCE: 84
gcacccaact ctcatacatt cc                                   22

<210> SEQ ID NO 85
<211> LENGTH: 15
<212> TYPE: DNA
<213> ORGANISM: Artificial Sequence
<220> FEATURE:
<223> OTHER INFORMATION: synthetic QRT-PCR LPL probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (15)...(15)
<223> OTHER INFORMATION: c modified by minor-groove-binding
      non-fluorescent quencher (MGBNFQ)

<400> SEQUENCE: 85
tggctggacg gtaac                                           15

<210> SEQ ID NO 86
<211> LENGTH: 20
<212> TYPE: DNA
<213> ORGANISM: Artificial Sequence
<220> FEATURE:
<223> OTHER INFORMATION: synthetic QRT-PCR PLAC4 F primer

<400> SEQUENCE: 86
cctttccccc ttatccaact                                      20

<210> SEQ ID NO 87
<211> LENGTH: 22
<212> TYPE: DNA
<213> ORGANISM: Artificial Sequence
<220> FEATURE:
<223> OTHER INFORMATION: synthetic QRT-PCR PLAC4 R primer

<400> SEQUENCE: 87
gtactggttg ggctcatttt ct                                   22

<210> SEQ ID NO 88
<211> LENGTH: 15
<212> TYPE: DNA
<213> ORGANISM: Artificial Sequence
<220> FEATURE:
<223> OTHER INFORMATION: synthetic QRT-PCR PLAC4 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (15)...(15)
<223> OTHER INFORMATION: c modified by minor-groove-binding
      non-fluorescent quencher (MGBNFQ)

<400> SEQUENCE: 88
ccctagccta taccc                                               15

<210> SEQ ID NO 89
<211> LENGTH: 74
<212> TYPE: DNA
<213> ORGANISM: Artificial Sequence
<220> FEATURE:
<223> OTHER INFORMATION: synthetic QRT-PCR PLAC4 calibrator

<400> SEQUENCE: 89
cacctttccc ccttatccaa ctagccctag cctatacect ctgctgccca agaaaatgag    60
cccaaccagt acac                                                74

<210> SEQ ID NO 90
<211> LENGTH: 18
<212> TYPE: DNA
<213> ORGANISM: Artificial Sequence
<220> FEATURE:
<223> OTHER INFORMATION: synthetic QRT-PCR FN1 F primer

<400> SEQUENCE: 90
aagcaagccc ggttgtta                                            18

<210> SEQ ID NO 91
<211> LENGTH: 19
<212> TYPE: DNA
<213> ORGANISM: Artificial Sequence
<220> FEATURE:
<223> OTHER INFORMATION: synthetic QRT-PCR FN1 R primer

<400> SEQUENCE: 91
ccaacgcatt gcctaggta                                           19

<210> SEQ ID NO 92
<211> LENGTH: 20
<212> TYPE: DNA
<213> ORGANISM: Artificial Sequence
<220> FEATURE:
<223> OTHER INFORMATION: synthetic QRT-PCR FN1 probe
<220> FEATURE:
<221> NAME/KEY: modified_base
<222> LOCATION: (1)...(1)
<223> OTHER INFORMATION: a modified by FAM fluorescent reporter
<220> FEATURE:
<221> NAME/KEY: modified_base
<222> LOCATION: (20)...(20)
<223> OTHER INFORMATION: c modified by minor-groove-binding
      non-fluorescent quencher (MGBNFQ)

<400> SEQUENCE: 92
acactatcag ataaatcaac                                          20

<210> SEQ ID NO 93
<211> LENGTH: 85
<212> TYPE: DNA
<213> ORGANISM: Artificial Sequence
<220> FEATURE:
<223> OTHER INFORMATION: synthetic QRT-PCR FN1 calibrator

<400> SEQUENCE: 93
aaagcaagcc cggttgttat gacaatggaa aacactatca gataaatcaa cagtgggagc    60
ggacctacct aggcaatgcg ttggt                                    85

```
<210> SEQ ID NO 94
<211> LENGTH: 16
<212> TYPE: DNA
<213> ORGANISM: Artificial Sequence
<220> FEATURE:
<223> OTHER INFORMATION: synthetic QRT-PCR INHBA F primer

<400> SEQUENCE: 94
cgccctccca aaggat                                                       16

<210> SEQ ID NO 95
<211> LENGTH: 23
<212> TYPE: DNA
<213> ORGANISM: Artificial Sequence
<220> FEATURE:
<223> OTHER INFORMATION: synthetic QRT-PCR INHBA R primer

<400> SEQUENCE: 95
gcatgtttaa aatgtgcttc ttg                                               23

<210> SEQ ID NO 96
<211> LENGTH: 26
<212> TYPE: DNA
<213> ORGANISM: Artificial Sequence
<220> FEATURE:
<223> OTHER INFORMATION: synthetic QRT-PCR INHBA probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (26)...(26)
<223> OTHER INFORMATION: g modified by TAMRA fluorescent quencher

<400> SEQUENCE: 96
tacccaactc tcagccagag atggtg                                            26

<210> SEQ ID NO 97
<211> LENGTH: 76
<212> TYPE: DNA
<213> ORGANISM: Artificial Sequence
<220> FEATURE:
<223> OTHER INFORMATION: synthetic QRT-PCR INHBA calibrator

<400> SEQUENCE: 97
ccgccctccc aaaggatgta cccaactctc agccagagat ggtggaggcc gtcaagaagc       60
acattttaaa catgct                                                       76

<210> SEQ ID NO 98
<211> LENGTH: 20
<212> TYPE: DNA
<213> ORGANISM: Artificial Sequence
<220> FEATURE:
<223> OTHER INFORMATION: synthetic QRT-PCR LEP F primer

<400> SEQUENCE: 98
ggtgagagct gctctggaaa                                                   20

<210> SEQ ID NO 99
<211> LENGTH: 21
<212> TYPE: DNA
<213> ORGANISM: Artificial Sequence
<220> FEATURE:
<223> OTHER INFORMATION: synthetic QRT-PCR LEP R primer

<400> SEQUENCE: 99
```
cctcagcctg attaggtggt t                                          21

<210> SEQ ID NO 100
<211> LENGTH: 14
<212> TYPE: DNA
<213> ORGANISM: Artificial Sequence
<220> FEATURE:
<223> OTHER INFORMATION: synthetic QRT-PCR LEP probe
<220> FEATURE:
<221> NAME/KEY: modified_base
<222> LOCATION: (1)...(1)
<223> OTHER INFORMATION: t modified by FAM fluorescent reporter
<220> FEATURE:
<221> NAME/KEY: modified_base
<222> LOCATION: (14)...(14)
<223> OTHER INFORMATION: c modified by minor-groove-binding
      non-fluorescent quencher (MGBNFQ)

<400> SEQUENCE: 100
tgacccagat cctc                                                  14

<210> SEQ ID NO 101
<211> LENGTH: 62
<212> TYPE: DNA
<213> ORGANISM: Artificial Sequence
<220> FEATURE:
<223> OTHER INFORMATION: synthetic QRT-PCR LEP calibrator

<400> SEQUENCE: 101
gggtgagagc tgctctggaa aatgtgaccc agatcctcac aaccacctaa tcaggctgag  60
gt                                                               62

<210> SEQ ID NO 102
<211> LENGTH: 24
<212> TYPE: DNA
<213> ORGANISM: Artificial Sequence
<220> FEATURE:
<223> OTHER INFORMATION: synthetic QRT-PCR ADAM12 F primer

<400> SEQUENCE: 102
tggaaagaaa tgaaggtctc attg                                       24

<210> SEQ ID NO 103
<211> LENGTH: 19
<212> TYPE: DNA
<213> ORGANISM: Artificial Sequence
<220> FEATURE:
<223> OTHER INFORMATION: synthetic QRT-PCR ADAM12 R primer

<400> SEQUENCE: 103
tcgagcgagg gagacatca                                             19

<210> SEQ ID NO 104
<211> LENGTH: 29
<212> TYPE: DNA
<213> ORGANISM: Artificial Sequence
<220> FEATURE:
<223> OTHER INFORMATION: synthetic QRT-PCR ADAM12 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (29)...(29)
<223> OTHER INFORMATION: a modified by TAMRA fluorescent quencher

<400> SEQUENCE: 104

```
cacggaaacc cactatctgc aagacggta                                           29

<210> SEQ ID NO 105
<211> LENGTH: 84
<212> TYPE: DNA
<213> ORGANISM: Artificial Sequence
<220> FEATURE:
<223> OTHER INFORMATION: synthetic QRT-PCR ADAM12 calibrator

<400> SEQUENCE: 105
tggaaagaaa tgaaggtctc attgccagca gtttcacgga aacccactat ctgcaagacg        60
gtactgatgt ctccctcgct cgaa                                                84

<210> SEQ ID NO 106
<211> LENGTH: 21
<212> TYPE: DNA
<213> ORGANISM: Artificial Sequence
<220> FEATURE:
<223> OTHER INFORMATION: synthetic QRT-PCR PAPPA2 F primer

<400> SEQUENCE: 106
cacagtggaa gcctgggtta a                                                   21

<210> SEQ ID NO 107
<211> LENGTH: 22
<212> TYPE: DNA
<213> ORGANISM: Artificial Sequence
<220> FEATURE:
<223> OTHER INFORMATION: synthetic QRT-PCR PAPPA2 R primer

<400> SEQUENCE: 107
atcaaacaca cctgcgatga tg                                                  22

<210> SEQ ID NO 108
<211> LENGTH: 24
<212> TYPE: DNA
<213> ORGANISM: Artificial Sequence
<220> FEATURE:
<223> OTHER INFORMATION: synthetic QRT-PCR PAPPA2 probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (24)...(24)
<223> OTHER INFORMATION: a modified by TAMRA fluorescent quencher

<400> SEQUENCE: 108
ccggagggag gacagaacaa ccca                                                24

<210> SEQ ID NO 109
<211> LENGTH: 72
<212> TYPE: DNA
<213> ORGANISM: Artificial Sequence
<220> FEATURE:
<223> OTHER INFORMATION: synthetic QRT-PCR PAPPA2 calibrator

<400> SEQUENCE: 109
tcacagtgga agcctgggtt aaaccggagg gaggacagaa caacccagcc atcatcgcag        60
gtgtgtttga ta                                                             72

<210> SEQ ID NO 110
<211> LENGTH: 19
<212> TYPE: DNA
<213> ORGANISM: Artificial Sequence
```

```
<220> FEATURE:
<223> OTHER INFORMATION: synthetic QRT-PCR PAPPA F primer

<400> SEQUENCE: 110
gggcattcac accatcagt                                              19

<210> SEQ ID NO 111
<211> LENGTH: 21
<212> TYPE: DNA
<213> ORGANISM: Artificial Sequence
<220> FEATURE:
<223> OTHER INFORMATION: synthetic QRT-PCR PAPPA R primer

<400> SEQUENCE: 111
tcggtctgtc ttcaaggaga a                                           21

<210> SEQ ID NO 112
<211> LENGTH: 27
<212> TYPE: DNA
<213> ORGANISM: Artificial Sequence
<220> FEATURE:
<223> OTHER INFORMATION: synthetic QRT-PCR PAPPA probe
<220> FEATURE:
<221> NAME/KEY: modified_base
<222> LOCATION: (1)...(1)
<223> OTHER INFORMATION: c modified by FAM fluorescent reporter
<220> FEATURE:
<221> NAME/KEY: modified_base
<222> LOCATION: (27)...(27)
<223> OTHER INFORMATION: t modified by TAMRA fluorescent quencher

<400> SEQUENCE: 112
ccaagacaac aaagacccac gctactt                                     27

<210> SEQ ID NO 113
<211> LENGTH: 72
<212> TYPE: DNA
<213> ORGANISM: Artificial Sequence
<220> FEATURE:
<223> OTHER INFORMATION: synthetic QRT-PCR PAPPA calibrator

<400> SEQUENCE: 113
tgggcattca caccatcagt gaccaagaca acaaagaccc acgctacttt ttctccttga  60
agacagaccg ag                                                     72
```